(12) United States Patent  (10) Patent No.: US 7,915,315 B2
Lynch et al.  (45) Date of Patent: Mar. 29, 2011

(54) BENZOCYCLOHEPTYL ANALOGS HAVING SPHINGOSINE 1-PHOSPHATE RECEPTOR ACTIVITY

(75) Inventors: Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/470,017

(22) Filed: May 21, 2009

(65) Prior Publication Data

US 2009/0253761 A1   Oct. 8, 2009

Related U.S. Application Data

(63) Continuation of application No. PCT/US2007/085433, filed on Nov. 21, 2007.

(60) Provisional application No. 60/860,781, filed on Nov. 21, 2006, provisional application No. 60/956,354, filed on Aug. 16, 2007.

(51) Int. Cl.
*A61K 31/185* (2006.01)
*A61K 31/135* (2006.01)
*C07C 211/02* (2006.01)
*C07C 215/20* (2006.01)

(52) U.S. Cl. ........ 514/577; 514/649; 564/336; 564/338; 564/339

(58) Field of Classification Search .................. 514/364, 514/577, 649, 681; 562/41; 564/338, 339; 568/327; 548/131
See application file for complete search history.

(56) References Cited

U.S. PATENT DOCUMENTS

| | | | |
|---|---|---|---|
| 3,153,092 A | 10/1964 | Burger | |
| 4,939,130 A | 7/1990 | Jaeggi et al. | |
| 5,405,988 A | 4/1995 | Klar et al. | |
| 6,069,251 A | 5/2000 | Thurkauf et al. | |
| 6,875,757 B2 | 4/2005 | Miller et al. | |
| 7,060,697 B2 | 6/2006 | Marsilje et al. | |
| 7,064,217 B2 | 6/2006 | Macdonald et al. | |
| 7,241,790 B2 | 7/2007 | Lynch et al. | |
| 7,638,637 B2 | 12/2009 | Lynch et al. | |
| 2004/0224941 A1 | 11/2004 | Seko et al. | |
| 2005/0032744 A1 | 2/2005 | Michaelis et al. | |
| 2005/0043386 A1 | 2/2005 | Nishi et al. | |
| 2005/0107447 A1 | 5/2005 | Lynch et al. | |
| 2006/0046979 A1 | 3/2006 | Foster et al. | |
| 2006/0122181 A1 | 6/2006 | Ikemoto et al. | |
| 2006/0135786 A1 | 6/2006 | Saha et al. | |
| 2006/0211656 A1 | 9/2006 | Albert et al. | |
| 2006/0223866 A1 | 10/2006 | Evindar et al. | |
| 2007/0191313 A1 | 8/2007 | Beard et al. | |
| 2008/0249070 A1 | 10/2008 | Lynch et al. | |
| 2009/0042955 A1 | 2/2009 | Lynch et al. | |
| 2009/0062238 A1 | 3/2009 | Lynch et al. | |
| 2009/0105315 A1 | 4/2009 | Lynch et al. | |
| 2009/0137531 A1 | 5/2009 | Lynch et al. | |
| 2009/0253759 A1 | 10/2009 | Lynch et al. | |
| 2009/0253760 A1 | 10/2009 | Lynch et al. | |

FOREIGN PATENT DOCUMENTS

| | | |
|---|---|---|
| DE | 1 056 139 | 4/1959 |
| DE | 3 544 373 A1 | 6/1987 |
| EP | 1 553 091 A1 | 7/2005 |
| EP | 1 602 660 A1 | 12/2005 |
| GB | 950388 | 2/1964 |
| JP | 1994 135935 | 5/1994 |
| JP | 1994 135936 | 5/1994 |
| JP | 2002 316985 | 10/2002 |
| JP | 2004 307442 | 4/2004 |
| WO | WO 99/35259 | 7/1999 |
| WO | WO 01/60819 A1 | 8/2001 |
| WO | WO 01/71022 A2 | 9/2001 |
| WO | WO 02/076995 A2 | 10/2002 |
| WO | WO 02/092068 A1 | 11/2002 |
| WO | WO 03/059880 A1 | 7/2003 |
| WO | WO 03/061567 A2 | 7/2003 |
| WO | WO 2004/010987 A2 | 2/2004 |
| WO | WO 2004/017917 A2 | 3/2004 |
| WO | WO 2004/024673 A1 | 3/2004 |
| WO | WO 2004/028521 A2 | 4/2004 |
| WO | WO 2004/047743 A2 | 6/2004 |
| WO | WO 2004/096752 A1 | 11/2004 |
| WO | WO 2004/096757 A1 | 11/2004 |
| WO | WO 2004/103279 A2 | 12/2004 |
| WO | WO 2004/103306 A2 | 12/2004 |
| WO | WO 2005/032465 A2 | 4/2005 |
| WO | WO 2005/118523 A1 | 12/2005 |
| WO | WO 2006/001463 A1 | 1/2006 |
| WO | WO 2006/020951 A1 | 2/2006 |
| WO | WO 2007/085451 A2 | 8/2007 |
| WO | WO 2007/086001 A2 | 8/2007 |
| WO | WO 2007/091396 A1 | 8/2007 |
| WO | WO 2008-079382 | 7/2008 |
| WO | WO 2009/023854 A1 | 2/2009 |
| WO | WO 2009/043013 A2 | 4/2009 |
| WO | WO 2009/146112 A2 | 12/2009 |

OTHER PUBLICATIONS

International Search Report for PCT/US2007/085433, Aug. 2008.
Bandini, M. et al., *Eur. J. Chem.* 2001, 1937-1942.
Beilstein, Registry No. 6240345, 1985.
Bertus, P. et al., *Chem Commun*, 2001, 1792-1793.
Brinkmann, V. et al., *Transplantation* 72, 2001, 764-769.
Brinkmann, V. et al., *J Biol Chem* 277, 2002, 21453-21457.
Burger, A. et al., *Journal of Medicine and Pharmaceutical Chemistry*, vol. 4, No. 3, 1961.
Chiba, K. et al., *J Immunol* 160, 1998, 5037-5044.
Choi, D. et al., *J Med Chem* 39, 1996, 1907-1916.

(Continued)

*Primary Examiner* — Kamal A Saeed
*Assistant Examiner* — Kristin Bianchi
(74) *Attorney, Agent, or Firm* — Rodney L. Sparks

(57) ABSTRACT

Benzocycloheptyl analogs that have agonist activity at one or more of the S1P receptors are provided. The compounds are sphingosine analogs, which, after phosphorylation, can behave as agonists at S1P receptors.

13 Claims, 13 Drawing Sheets

OTHER PUBLICATIONS

Clair, T. et al., *Cancer Res* 63, 2003, 5446-5453.
Clemens, J. et al., *Bioorg Med Chem Lett* (2003), 3401-3404.
Clemens, J. et al., *Bioorg. & Med. Chem. Lett.* (2004), 4903-4906.
Clemens, J. et al., *Bioorg. & Med. Chem. Lett.* (2005), 2005, 3568-3572.
Crosignani, S. et al., *Tetrahedron* 54, (1998), 15721-15730.
Davis, M. et al., *The J. of Bio. Chem.*, (2005), 9833-9841.
Dworkin, R. H. et al., *Arch. Neurol.*, 60, 2003, p1524-1534.
Forrest, M. et al., *J Pharmacol Exp Ther* 309, 2004, 758-768.
Foss, F. et al., *Bioorganic & Medicinal Chemistry* 15, 2005, 4470-4474.
Foss, F. et al., *Bioorganic & Medicinal Chemistry* 15, 2007, 663-677.
Fujino, M. et al., *J Pharmacol Exp Ther* 305, 2003, 70-77.
Graler, M. H. et al., *FASEB* 18, 2004, 551-553.
Hale, Jeffrey J. et al., *Bioorganic & Medicinal Chemistry Letters* 14, 2004, 3351-3355.
Hale, J. J. et al., 2004 *Bioorg Med Chem Lett* 14, 2004, 3501-3505.
Hale, J. J. et al., (2004) *Bioorg Med Chem Lett* 14, 3495-3499.
Hale, J. J. et al., *J Med Chem*, 2004, 47, 6662-6665.
Hanessian, S. et al., *Bioorganic & Medicinal Chemistry Letters* 17, 2007, 491-494.
Hoshino, Y. et al., (1999) *Transplant Proc* 31, 1224-1226.
Im, D. S. et al., (2000) *J Biol Chem* 275, 14281-14286.
Im, D. S. et al., *Biochemistry* 40, 2001, 14053-14060.
Jones, L. et al., (1997) *J Org Chem* 62, 1388-1410.
Kaiser, C. et al., XP009032189, Nov. 1962, 1243-1265.
Kawasaki, K. et al., *Tetrahedron*, vol. 53, No. 18, 1997, 6337-6350.
Kharel, Y. et al., *J Bio Chem*, vol. 280, No. 44, Nov. 4, 2005, 3686536872.
Kimura, T. et al., (2003) *Arterioscler Thromb Vasc Biol* 23, 1283-1288.
Kiuchi, M. et al.,(2000) *J Med Chem* 43, 2946-2961.
Kon, J. et al., (1999) *J Biol Chem* 274, 23940-23947.
Kotera et al. Chem. Abst.: Registry Record 19352-04-6, 1968.
Lee, M. J. et al., (1998) *Science* 279, 1552-1555.
Lew, M. J. et al., "Analysis of competitive agonist-antagonist interactions by nonlinear regression", (1995) *Trends Pharmacol Sci* 16, 328-337.
Li, Z. et al., *Journal of Medicinal Chemistry*, vol. 48, No. 20, Oct. 6, 2005, 6169-6173.
Maki, T. et al., (2002) *Transplantation* 74, 1684-1686.
Maki, T. et al., (2005) *Transplantation* 79, 1051-1055.
Mandala, S. et al., (2002) *Science* 296, 346-349.
Matloubian, M. et al., (2004) *Nature* 427, 355-360.
Sanchez, T. et al., (2003) *J Biol Chem* 278, 47281-47290.
Sanna, M. G. et al., (2004) *J Biol Chem* 279, 13839-13848.
Sanna, M. G. et al., *Nature Chemical Biology*, vol. 2, Aug. 2006, 434-441.
Suzuki, S. et al., (1996) *Transpl Immunol* 4, 252-255.
Van Brocklyn, J. R. et al., (1999) *J Biol Chem* 274, 4626-4632.
Vogler, R. et al., (2005), No. 20, 2005, 6169-6173.
Xie, J. H. et al., (2003) *J Immunol* 170, 3662-3670.
Yanagawa, Y. et al., (2000) *Int J Immunopharmacol* 22, 597-602.
Yanagawa, Y. et al., (1999) *Transplant Proc* 31, 1227-1229.
Yang, Z., et al., (2003) *Clin Immunol* 107, 30-35.
Zhang, T. et al., (1997) *Cancer Res* 57, 169-175.
Zhang, Y. H. et al., *J Neurophysiol* 96, 2006, 1042-1052.
Zhang, Y. H. et al., *J Physiol* 575.1, 2006, 101-113.

FTY720

AAL151

XXIX

SCHEME 1
2,6-Benzocycloheptyl Compounds

Reagents and conditions: a) Tf$_2$O, 2,6-lutidine, CH$_2$Cl$_2$, 0°C, 2h, 90%; b) 1-octene, 9-BBN, K$_3$PO$_4$, KBr, H$_2$O, Pd(PPh$_3$)$_4$, 65°C, 2h, 72%; c) CuBr$_2$, EtOAc, CHCl$_3$, reflux 6h, 80%; d) NaH, N-acetamido-dimethylmalonate, DMF, 0°C-rt, overnight,15%; e) Et$_3$SH, TiCl$_4$,CH$_2$Cl$_2$, rt, 12h, 55%; f) LiBH$_4$, rt, THF, 48h, 33%; g) LiOH, H$_2$O, MeOH, THF, 50°C, 5h, 75%.

SCHEME 2A

Vinyl 2,6-Benzocycloheptyl Compounds

SCHEME 2B

Scheme 3
2,6-Benzocycloheptyl Compounds having Ring Heteroatoms

X = O, S, NH, NR (R = $C_1$ to $C_6$ alkyl), NC(O)R

Reagents and conditions: a) $Tf_2O$, 2,6-lutidine, $CH_2Cl_2$, 0°C, 2h, 90%; b) 1-octene, 9-BBN, $K_3PO_4$, KBr, $H_2O$, $Pd(PPh_3)_4$, 65°C, 2h, 72%; c) $CuBr_2$, EtOAc, $CHCl_3$, reflux 6h, 80%; d) NaH, N-acetamido-dimethylmalonate, DMF, 0°C-rt, overnight,15%; e) $Et_3SH$, $TiCl_4$,$CH_2Cl_2$, rt, 12h, 55%; f) $LiBH_4$, rt, THF, 48h, 33%; g) LiOH, $H_2O$, MeOH, THF, 50°C, 5h, 75%.

BENZOCYCLOHEPTYL ANALOGS HAVING SPHINGOSINE 1-PHOSPHATE RECEPTOR ACTIVITY

CROSS-REFERENCE TO RELATED APPLICATIONS

This application is a continuation of International Application PCT/US2007/085433 filed on Nov. 21, 2007 and published in English as WO 2008/064337 on May 29, 2008, which claims priority to Provisional Application Nos. 60/956,354, filed Aug. 16, 2007 and Application Ser. No. 60/860,781, filed Nov. 21, 2006, the disclosures of all of which are incorporated by reference in their entirety.

US GOVERNMENT RIGHTS

This invention was made with United States Government support under Grant No. RO1 GM 067958 awarded by the National Institutes of Health. The United States Government has certain rights in the invention.

BACKGROUND OF THE INVENTION

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl)ethyl]propane 1,3-diol), that following phosphorylation, is an agonist at 4 of 5 S1P receptors, revealed that enhancing S1P tone influences lymphocyte trafficking. Further, S1P type 1 receptor ($S_1P_1$) antagonists cause leakage of the lung capillary endothelium, which suggests that S1P may be involved in maintaining the integrity of the endothelial barrier in some tissue beds.

Sphingosine 1-phosphate (S1P) is a lysophospholipid mediator that evokes a variety of cellular responses by stimulation of five members of the endothelial cell differentiation gene (EDG) receptor family.

Sphingosine-1-phosphate (S1P) has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing and tumor growth inhibition.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine 1-phosphate phosphohydrolases. Irreversible degradation of S1P is catalyzed by S1P lyase yielding ethanolamine phosphate and hexadecenal.

Currently, there is a need for novel, potent, and selective agents that are agonists of the S1P receptor having enhanced potency, selectivity, and oral bioavailability. In addition, there is a need in the art for identification of, as well as the synthesis and use of such compounds. The present invention satisfies these needs.

SUMMARY

The present invention provides in one aspect compounds that have agonist activity at one or more of the S1P receptors. The compounds are sphingosine analogs which, after phosphorylation, can behave as agonists at S1P receptors. Accordingly, there is provided compounds of Formula IA, IB, or IC:

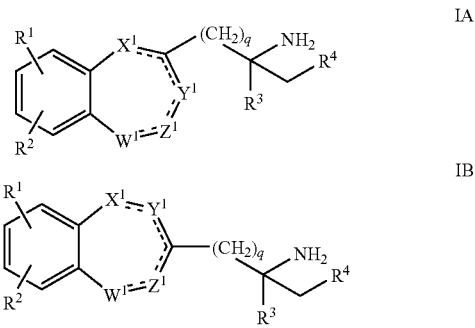

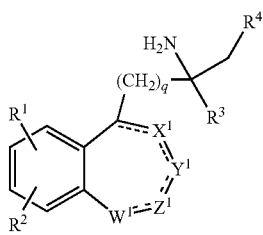

wherein $W^1$, $X^1$, $Y^1$ and $Z^1$ are independently O, $CR^a$, $CR^aR^b$, N, $NR^c$, or S.

$R^1$ and $R^2$ are independently hydrogen, halo, halo($C_1$-$C_{10}$)alkyl, cyano, —$NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl; or $R^2$ can be a group having Formula II, III, IV, V, or VI:

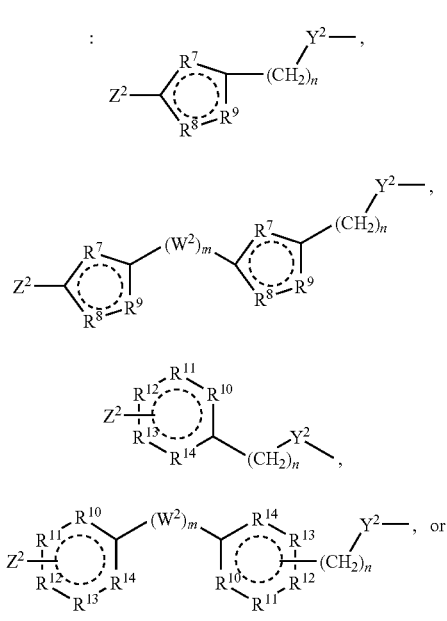

wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^{18}$; and each $R^5$, $R^{16}$ and $R^{17}$ is independently hydrogen, halo, ($C_1$-$C_{10}$)alkyl, ($C_6$-$C_{10}$)aryl, ($C_1$-$C_{10}$)alkyl substituted with halo, hydroxy, ($C_1$-$C_{10}$)alkoxy, or cyano; and where $R^{18}$ can be hydrogen or ($C_1$-$C_{10}$)alkyl;

$Z^2$ is hydrogen, halo, halo($C_1$-$C_{10}$)alkyl, cyano, —$NR^aR^b$, ($C_1$-$C_{20}$)alkyl, ($C_2$-$C_{20}$)alkenyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl. The alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $Z^2$ alkyl groups can be independently replaced with non-peroxide oxygen, sulfur or $NR^c$;

indicates one or more optional double bonds;

$Y^2$ is a bond (absent), O, S, C=O, or $NR^c$, $CH_2$; $W^2$ is a bond; —$CH_2$— and m is 1, 2, or 3, or (C=O)($CH_2$)$_{1-5}$ and m is 1; wherein $W^2$ is optionally interrupted with non-peroxide O, S, C=O, or $NR^c$. Each ---represents an optional double bond; n is 0, 1, 2, or 3 and q is 0, 1, 2, or 3.

$R^3$ is hydrogen, ($C_1$-$C_{10}$)alkyl, hydroxy($C_1$-$C_{10}$)alkyl or ($C_1$-$C_{10}$)alkoxy; and $R^4$ is hydroxy (—OH), phosphate (—$OPO_3H_2$), phosphonate (—$CH_2PO_3H_2$), or alpha-substituted phosphonate. Each $R^a$, $R^b$, $R^c$, and $R^d$ is independently hydrogen, or ($C_1$-$C_{10}$)alkyl.

The alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $R^1$ or $R^2$ alkyl groups can be independently replaced with non-peroxide oxygen, sulfur or $NR^c$. The alkyl groups of $R^3$ are optionally substituted with 1, or 2 hydroxy groups. The invention includes pharmaceutically acceptable salts or esters of the compounds of Formula IA, IB, or IC.

In another aspect, the invention provides phosphate monoesters having Formula VIIIA, VIIIB or VIIIC:

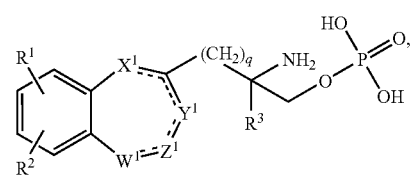

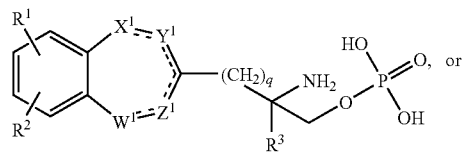

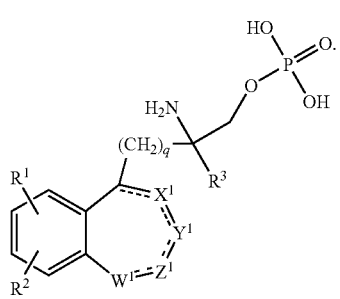

where $R^1$, $R^2$, $R^3$, $W^1$, $X^1$, $Y^1$, $Z^1$ and q are as defined above. In another aspect, the invention provides enantiomers and stereoisomers of the compounds having Formulas IA, IB, IC, VIIIA, VIIIB, or VIIIC.

In another aspect, the invention provides pro-drugs of the compounds of Formula IA, IB, or IC. The invention also provides compounds of Formula IA, IB, or pharmaceutically acceptable salts or esters thereof for use in medical therapy.

In another aspect, the present invention provides a method for inhibiting angiogenesis in a tumor, including contacting the cancerous cells with an effective amount of a compound of Formula IA, IB, IC, or a pharmaceutically acceptable salt or ester thereof.

In another aspect, the invention provides a method for modulating the immune system by altering lymphocyte trafficking for treatment of autoimmune diseases or prolongation of allograft transplant survival, said method includes administering to a subject in need thereof an effective amount of at least one compound of Formula IA, IB, IC, or a pharmaceutically acceptable salt or ester thereof.

In another aspect, the invention provides a method for preventing, inhibiting or treating neuropathic pain, wherein the method comprises administering an effective amount of at least one compound of Formula IA, IB, IC, or a compound of Formula IA, IB, or IC, and a pharmaceutically-acceptable carrier is administered to a subject in need thereof. Pain can be nociceptive or neuropathic in nature.

Neuropathic pain is characterized by its chronic nature, an absence of an obvious, direct cause (e.g., tissue damage), hyperalgesia or allodynia. Hyperalgesia is an exaggerated response to a painful stimulus. Allodynia is the perception of normal stimuli as painful (examples include the touch of clothing, warm or cool air, etc.). Neuropathic pain can be a sequel to nerve damage in an extremity such as an arm, or more often a leg. Precipitating events can include trauma, e.g., motor vehicle accidents or amputations (e.g., phantom limb pain). Neuropathic pain can occur due to an adverse effect of drug therapies, e.g., vincristine or paclitaxel (TAXOL™) or can occur as a component of disease pathologies, such as diabetes type 1 or type 2, shingles, HIV-1 infections, etc. Typically, neuropathic pain is not responsive to opiates or non-steroidal anti-inflammatory drugs such as aspirin.

In another aspect, the invention provides a method for repairing a vascular injury following catheterization, including contacting the lumen of the affected vessel with an effective amount of the compound of Formula IA, IB, or IC. In another aspect, the invention includes coating indwelling stents with a compound of Formula IA, IB, or IC.

In another aspect, the present invention provides compositions and methods for the use of S1P analogs to prevent and inhibit vascular restenosis following vascular injury. For example, the injury can be due to balloon angioplasty. In another aspect, the present invention includes a method for treating subjects to prevent vascular restenosis.

In another aspect, the present invention provides compositions and methods for the use of sphingosine analogs (including S1P pro-drugs) to prevent asthma attacks. In one aspect, the asthma could be due to over production of cysteinyl leukotrienes. In another aspect, the present invention includes a method for treating subjects to treat asthma.

In another aspect, the present invention provides compositions and methods for the use of sphingosine analogs of Formula IA, IB, or IC (including S1P pro-drugs) to treat obesity.

In another aspect, the present invention provides compositions and methods for the use of sphingosine analogs (including S1P pro-drugs) to normalize blood lipid composition. In one aspect, blood low density lipoprotein (LDL or 'bad cholesterol') levels could be lowered. In another aspect, blood triglyceride levels could be lowered.

In another aspect, the present invention provides compositions and methods for the use of S1P analogs and S1P pro-drugs for the prevention and treatment of arteriosclerosis.

In another aspect, the present invention provides compositions and methods for the use of S1P analogs and S1P pro-drugs for the treatment of neoplastic disease. In one aspect, this treatment is effected by application of S1P receptor antagonists that are efficacious by virtue of their anti-angiogenic properties. In another aspect, the treatment is effected by administration of sphingosine analogs of Formula IA, IB, or IC that inhibit the multiple substrate lipid kinase(s).

In another aspect, the present invention provides compositions and methods for the use of S1P analogs and S1P pro-drugs for the treatment of neurodegenerative diseases.

In one aspect, the treatment is for senile dementia of the Alzheimers type.

In another aspect, the invention provides a compound of Formula IA, IB, or IC, a pharmaceutically acceptable salt or ester thereof for use in medical treatment (for example, treatment of neoplastic disease, treatment of neuropathic pain, treatment of autoimmune disease, prolongation of allograft survival).

In another aspect, the invention provides a method for the use of a compound of Formula IA, IB, or IC or a pharmaceutically acceptable salt or ester thereof to prepare a medicament for inhibiting tumor growth, metastasis or tumor angiogenesis in a mammalian species (for example, a human).

In another aspect, the invention provides for the use of a compound of Formula IA, IB, or IC or a pharmaceutically acceptable salt or ester thereof to prepare a medicament for treating an autoimmune disease or prolonging allograft survival in a mammalian species (for example, a human).

In another aspect, the invention provides for the use of a compound of Formula IA, IB, or IC, or a pharmaceutically acceptable salt thereof to prepare a medicament for treating neuropathic pain in a mammalian species (for example, a human).

In another aspect, the invention provides a method for assessing a compound of Formula IA, IB, or IC (e.g., S1P receptor pro-drugs) as a substrate for sphingosine kinase types 1 or 2, in vitro and in vivo. In another aspect, the invention includes a method of assessing a compound of Formula IA, IB, or IC for binding to designated receptor sites including in vivo or in vitro, with an amount of a compound of Formula IA, IB, or IC effective to bind said receptors. Tissue having ligand bound designated S1P receptor sites can be used to measure the selectivity of test compounds for specific receptor subtypes, or can be used as a tool to identify potential therapeutic agents for the treatment of diseases, by contacting said agents with said ligand-receptor complexes, and measuring the extent of displacement of the ligand or binding of the agent.

In another aspect, the invention provides novel intermediates and processes disclosed herein that are useful for preparing compounds of Formula IA, IB, or IC, including the generic and specific intermediates as well as the synthetic processes described herein.

In another aspect, the present invention provides synthetic schemes and methods of use of compounds having Formula IA, IB, or IC and analogs or derivatives thereof. In another aspect, the invention provides synthetic and modification schemes for preparing analogs and derivatives of the compounds of Formula IA, IB, or IC, as well as compositions and methods for the use of such analogs and derivatives.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying description below. Other features, objects, and advantages of the invention will be apparent from the description and drawings, and from the claims.

DETAILED DESCRIPTION

Figure 1:
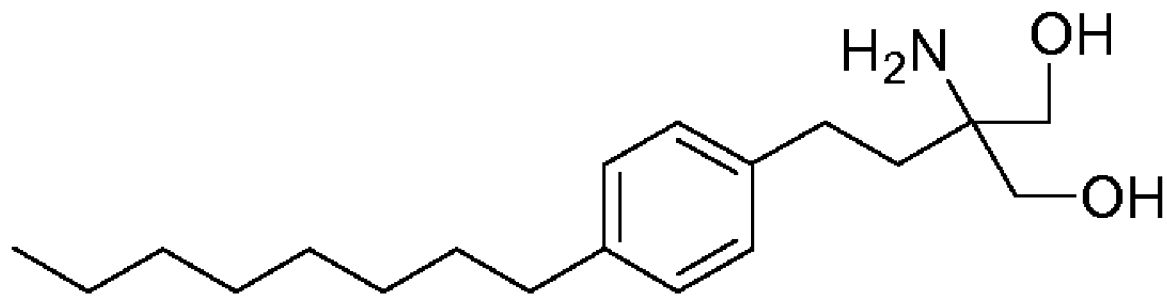
FIG. 1 illustrates three S1P agonists FTY720, AAL151 and compound XXIX.
Figure 1:
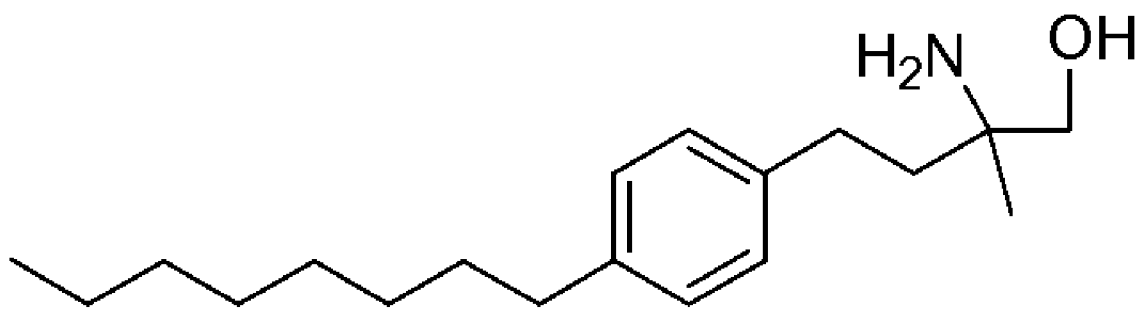
Figure 1:
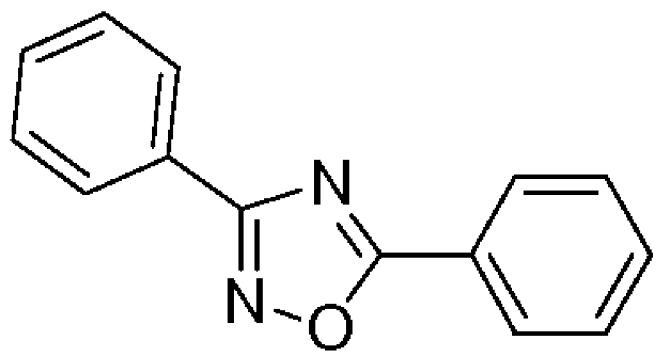
Figure 2A:
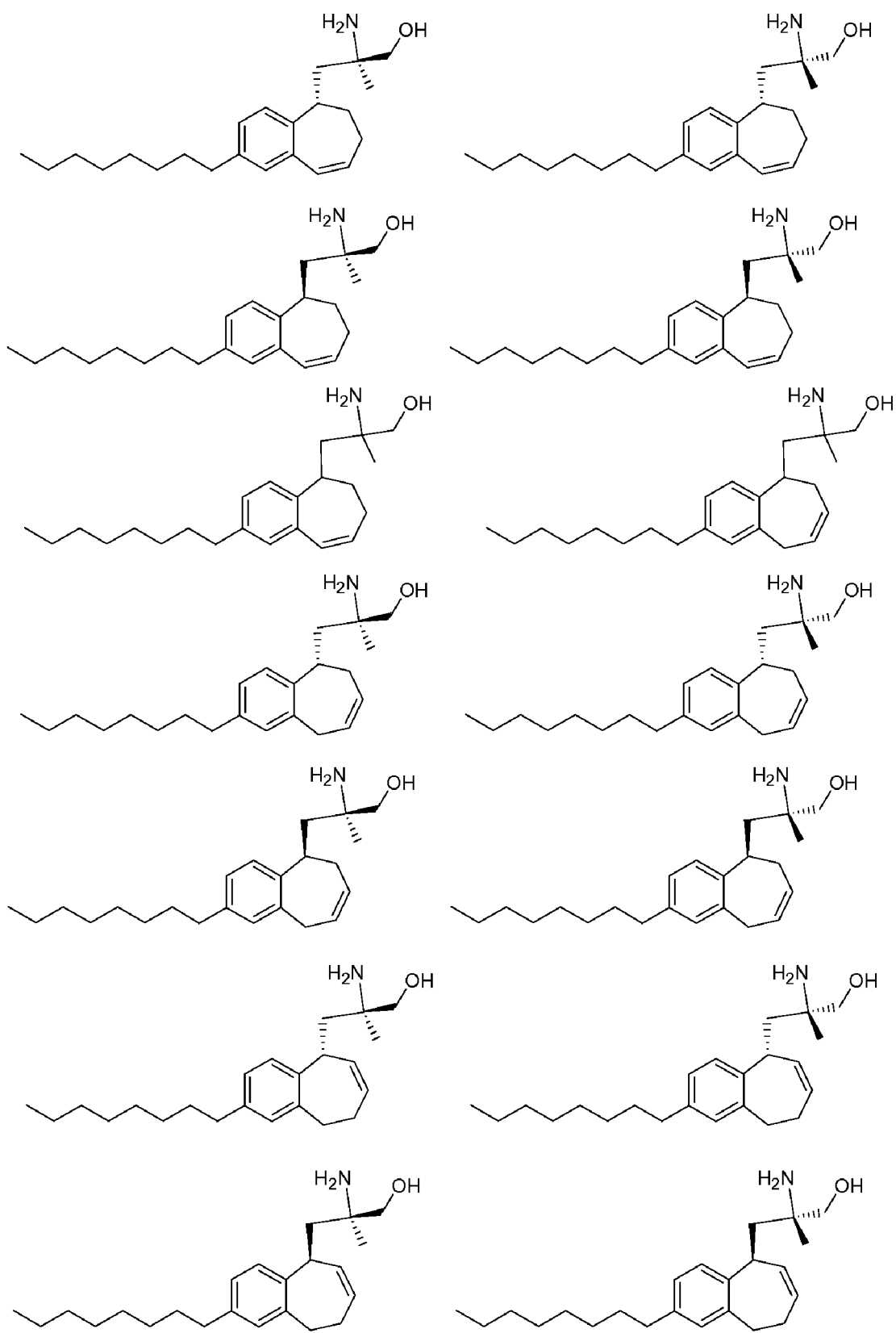
FIGS. 2A-2H illustrate additional compounds having Formula IA, IB, or IC.
Figure 2B:
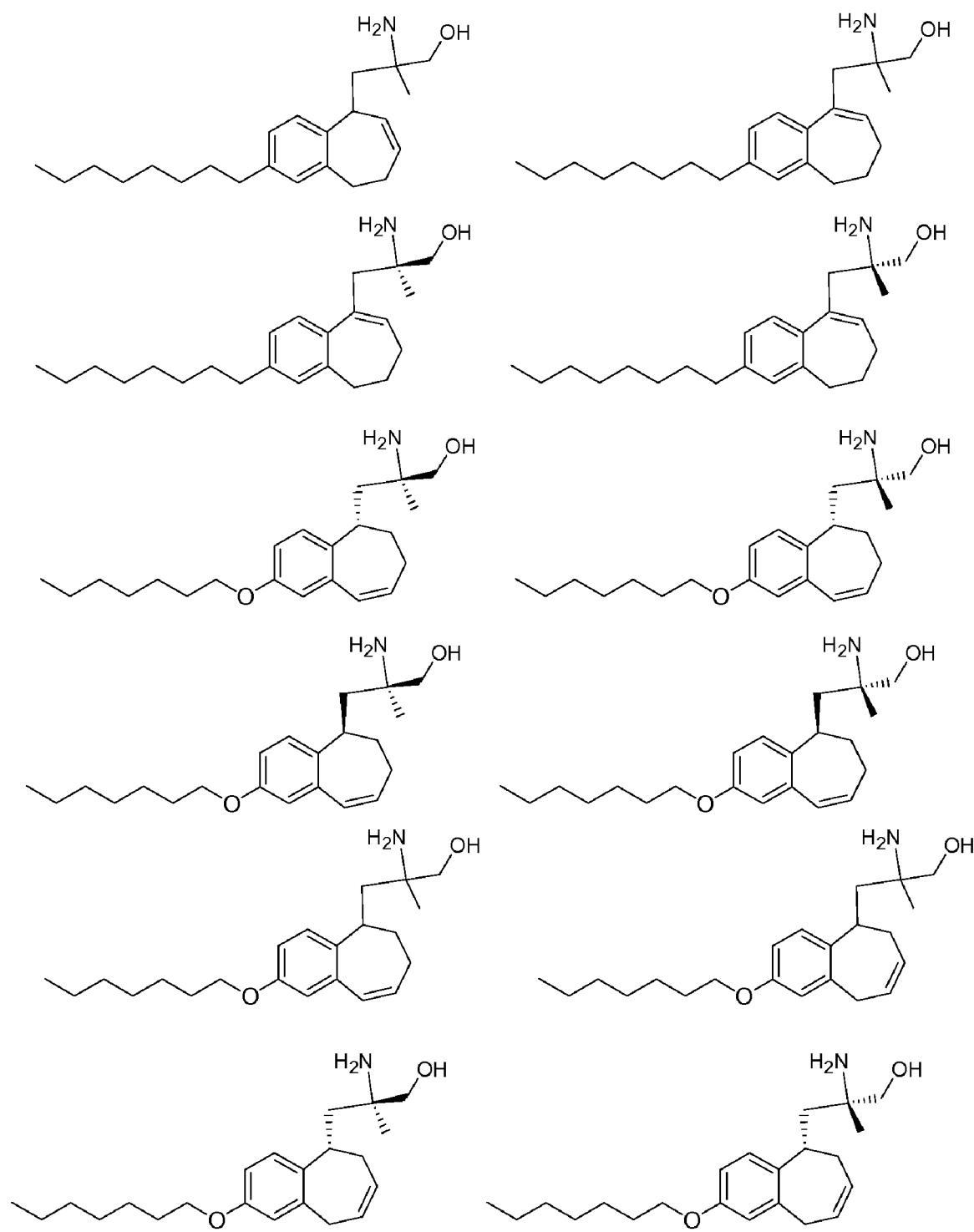
Figure 2C:
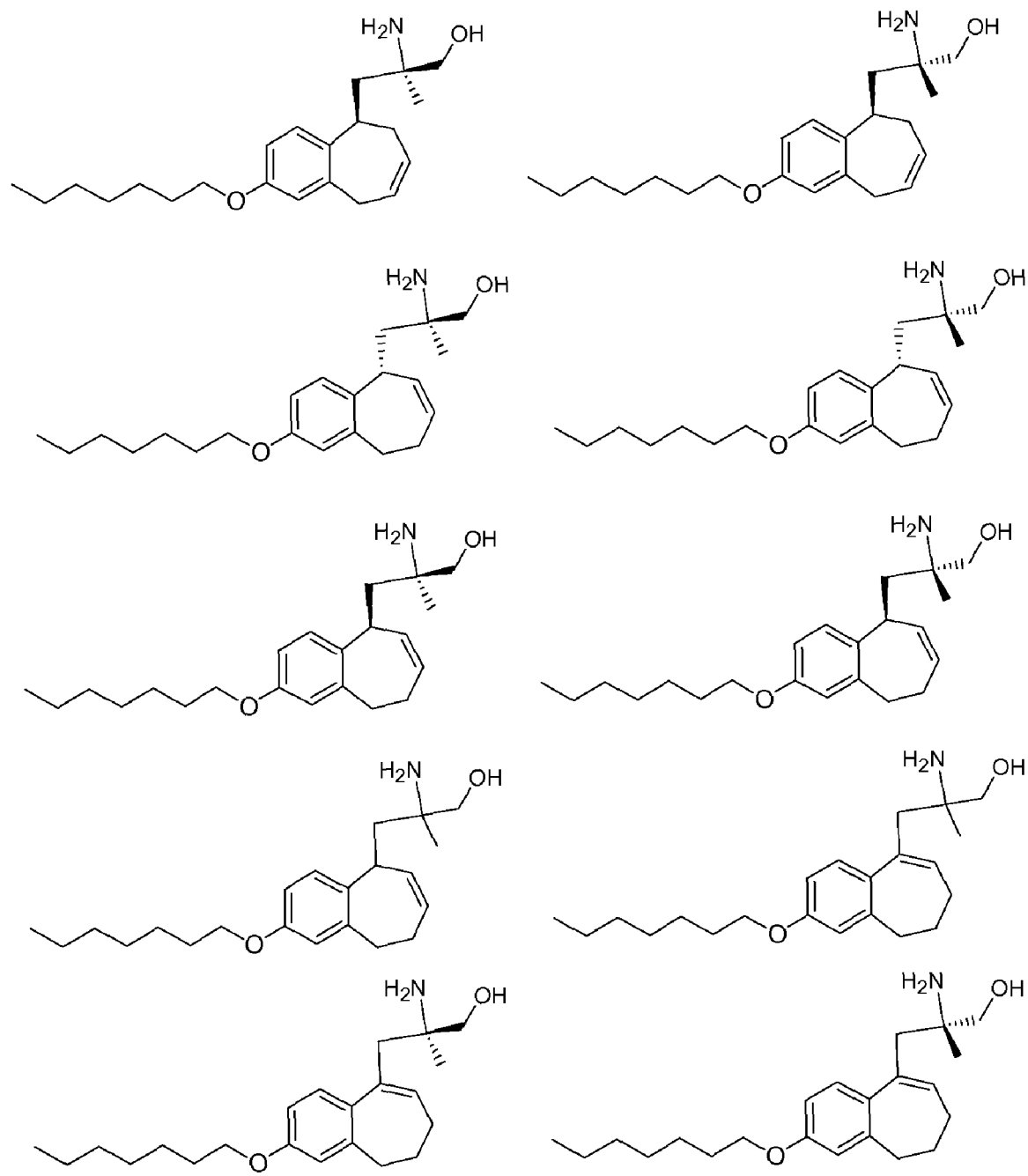
Figure 2D:
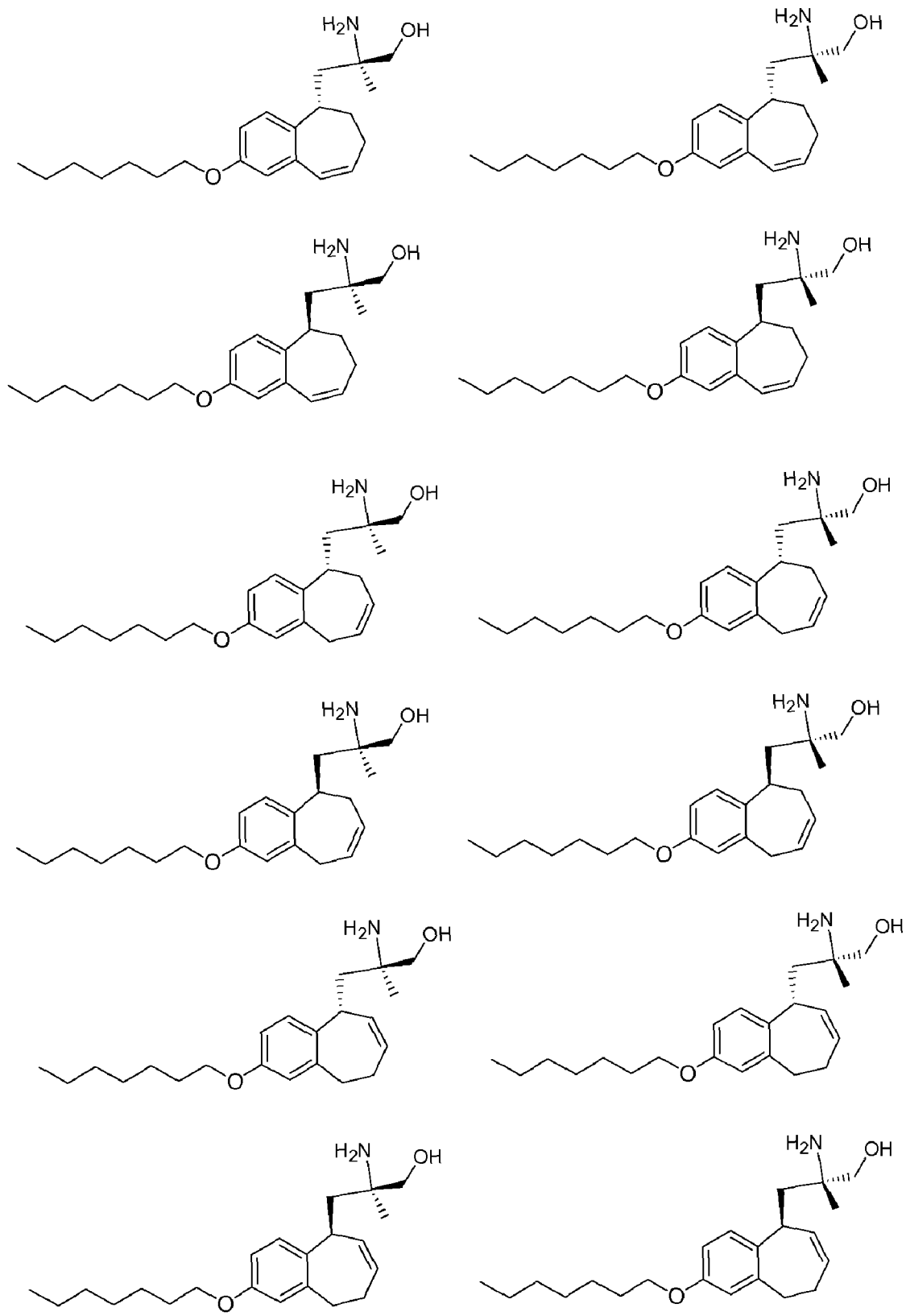
Figure 2E:
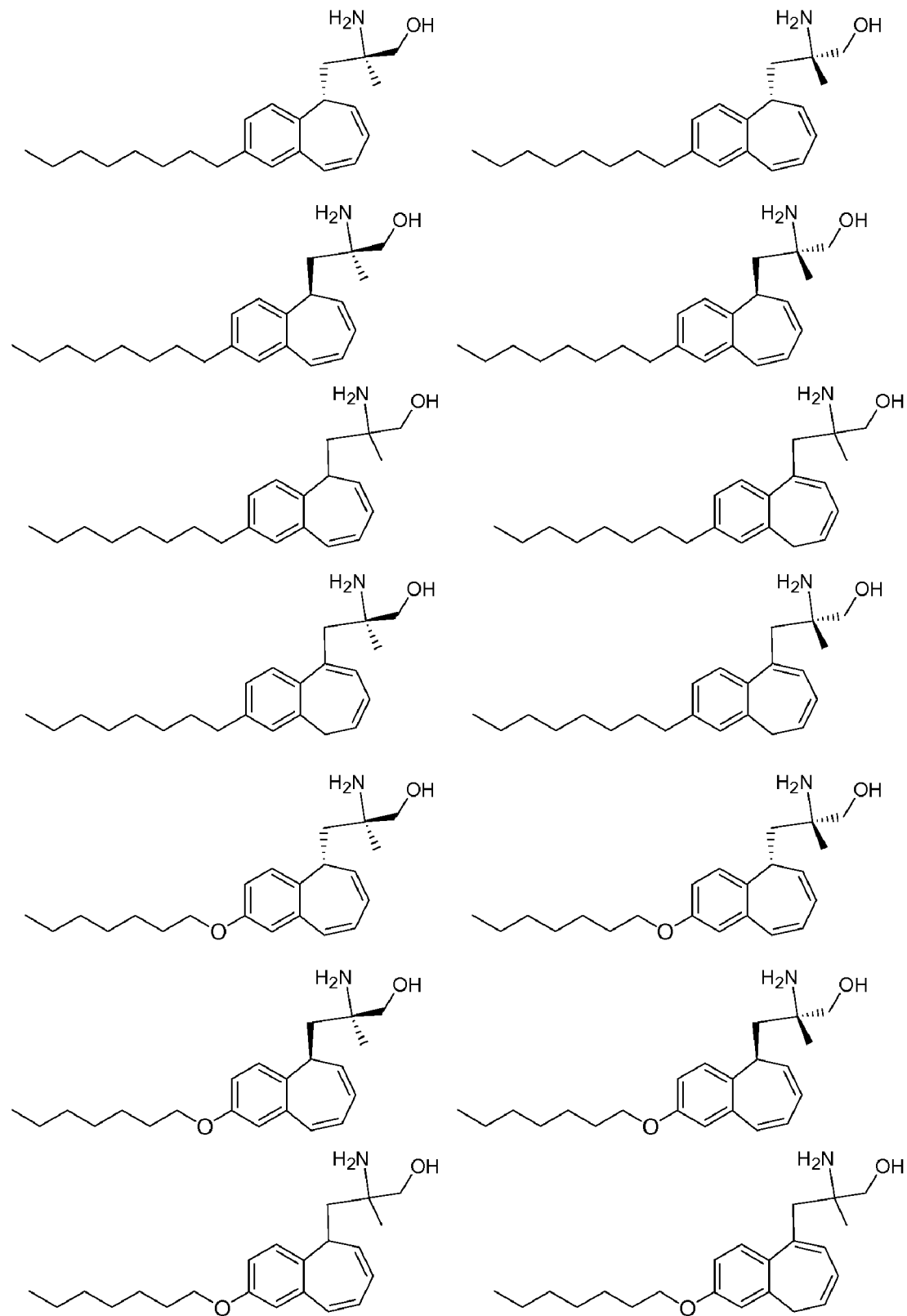
Figure 2F:
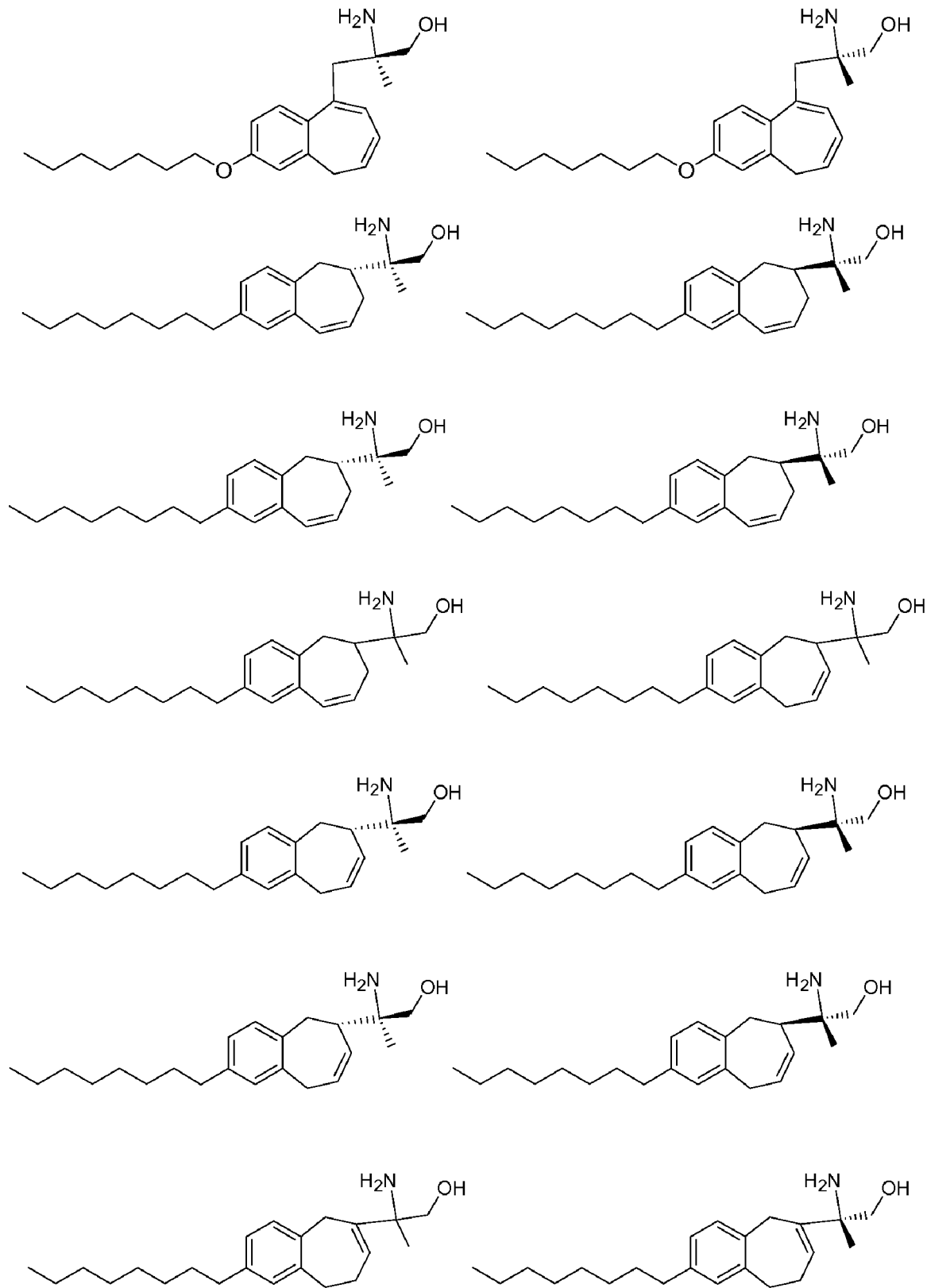
Figure 2G:
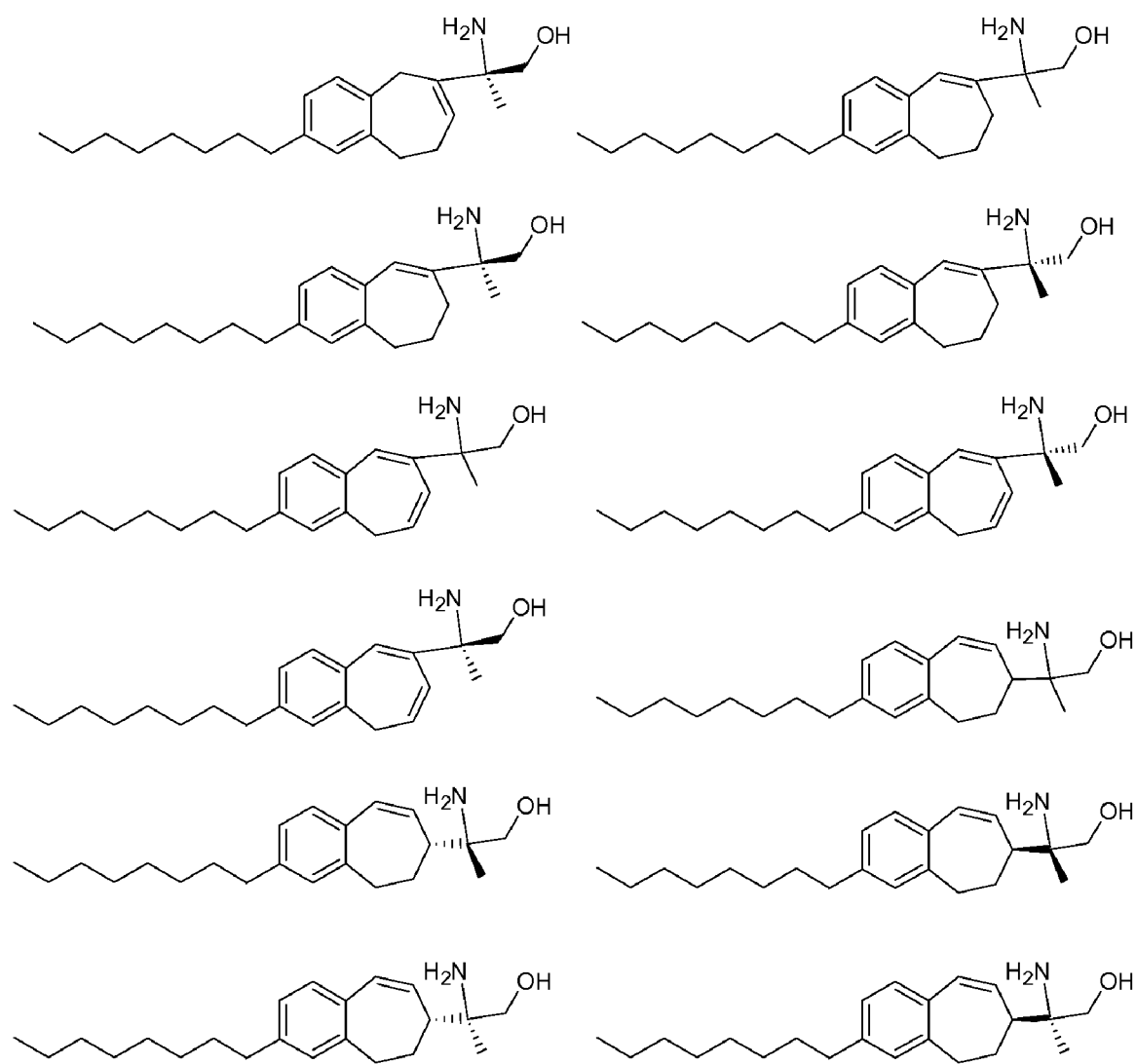
Figure 2H:
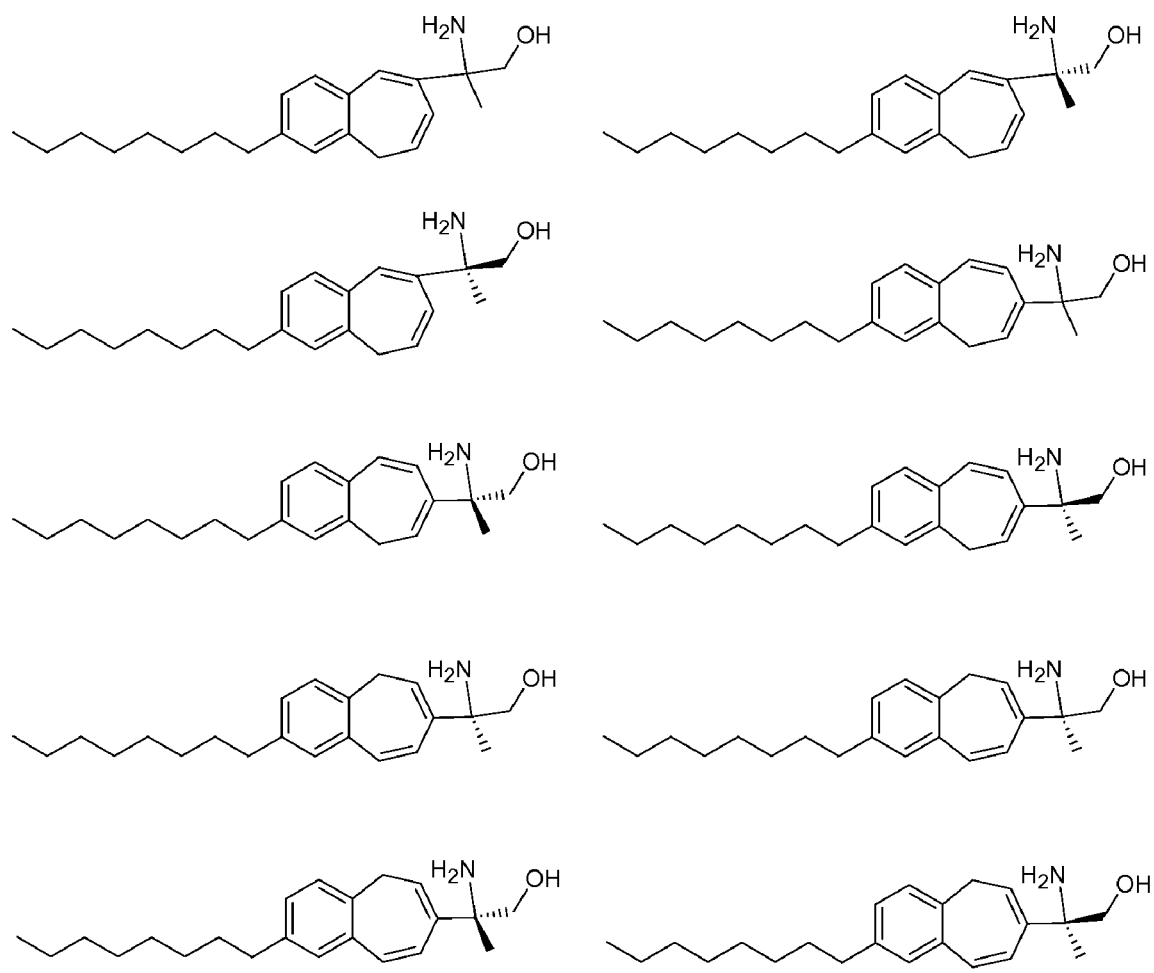
Figure 3:
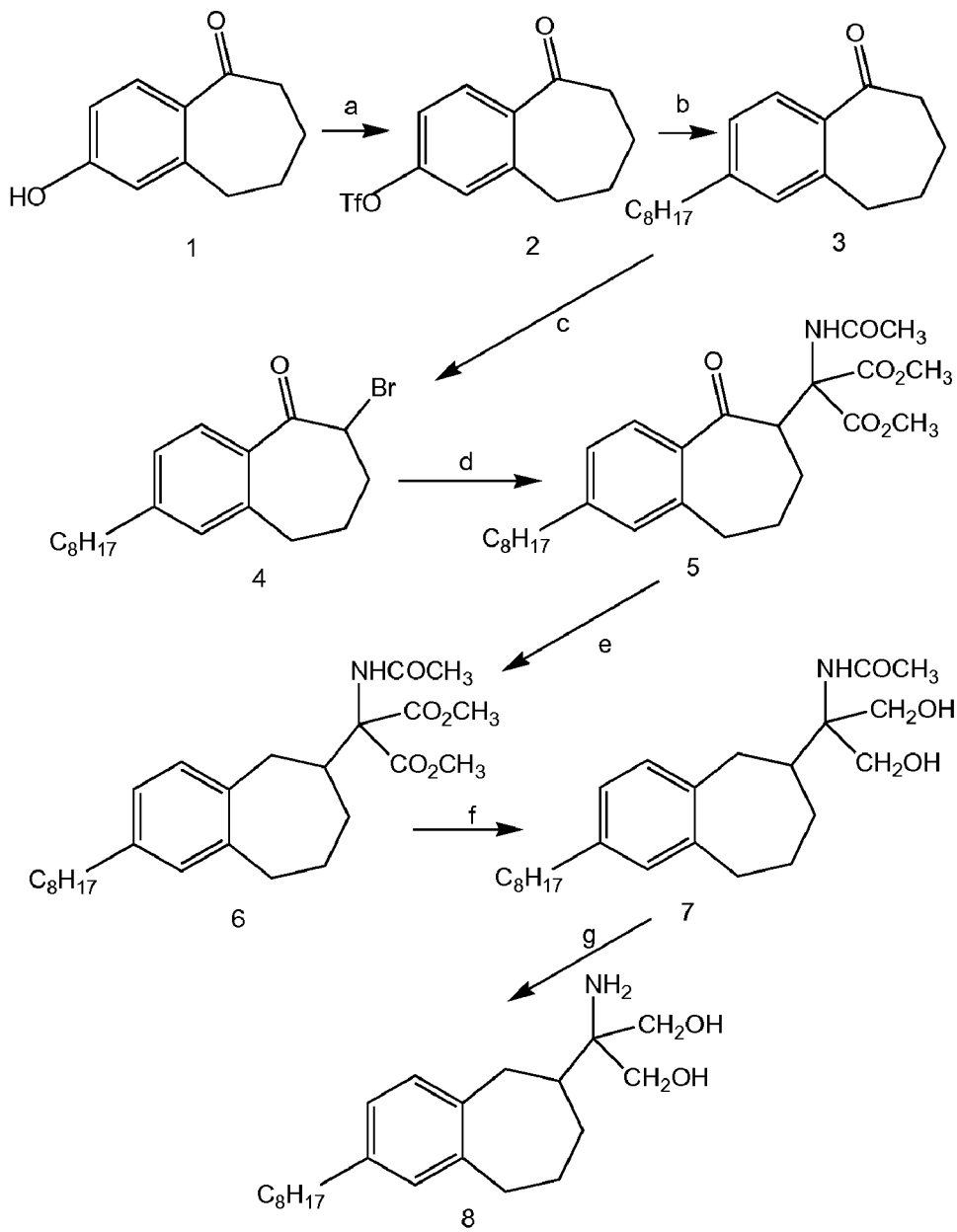
FIGS. 3-6 illustrate syntheses of compounds having Formula IA, IB, or IC.
Figure 4:
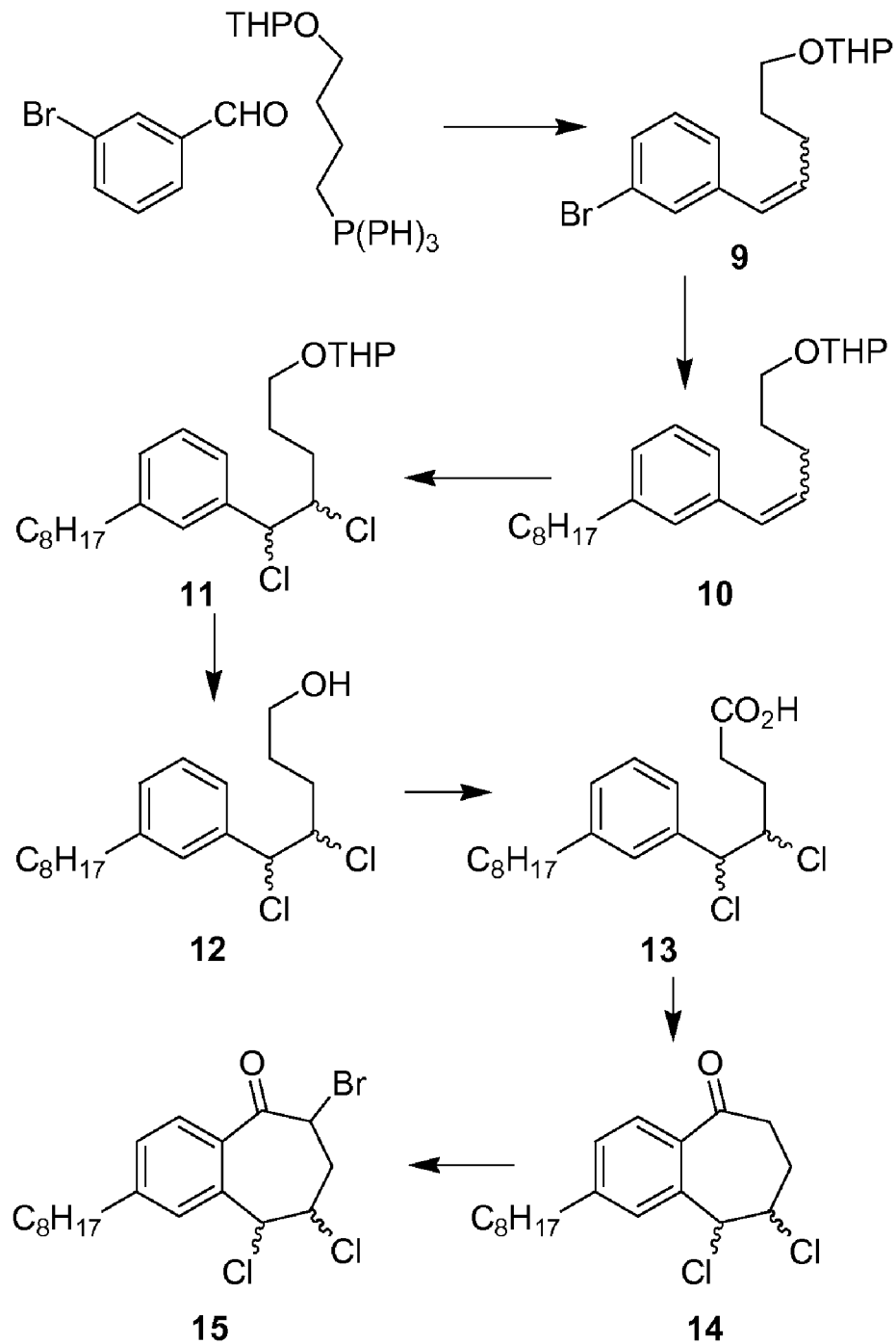
Figure 5:
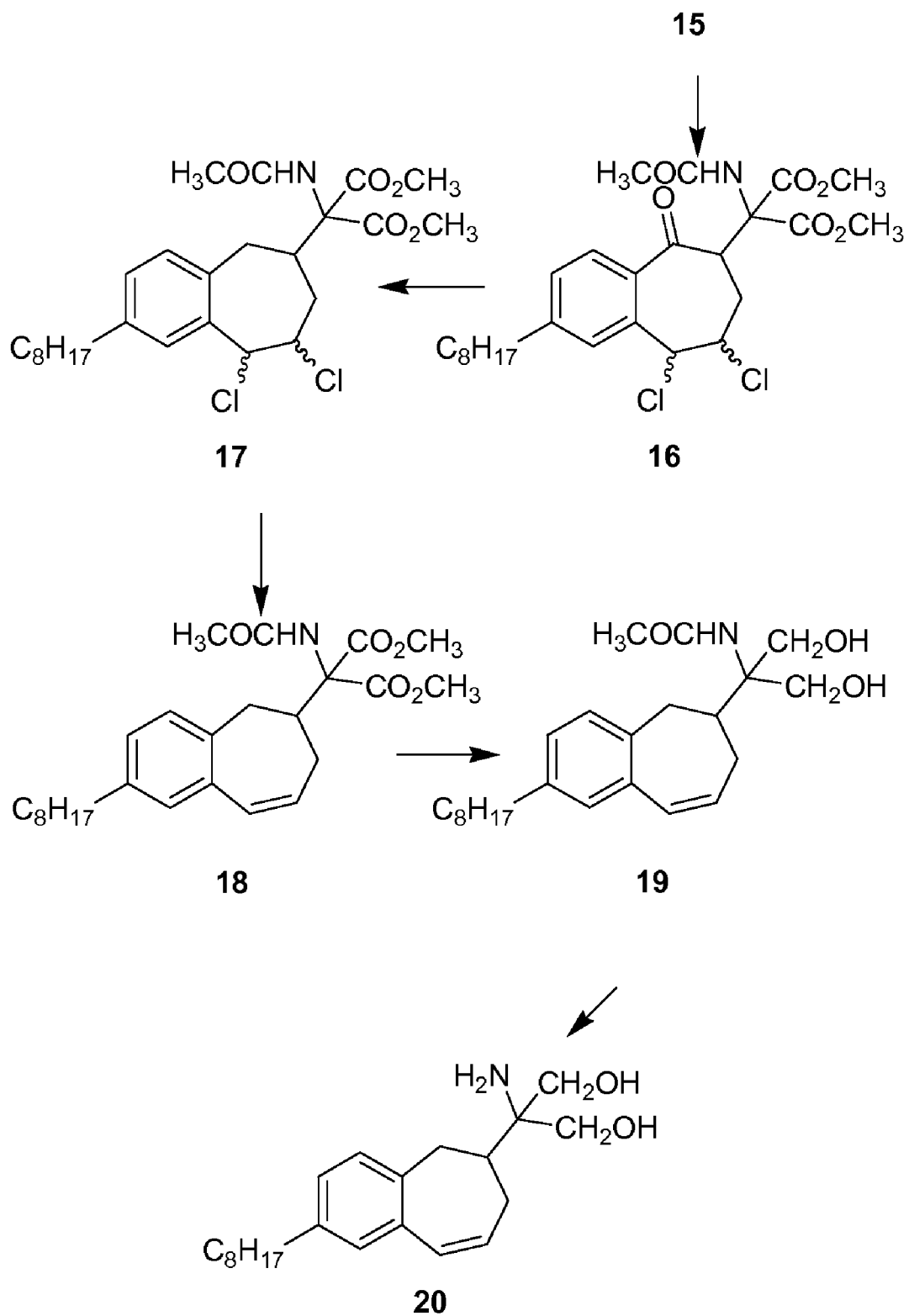
Figure 6:
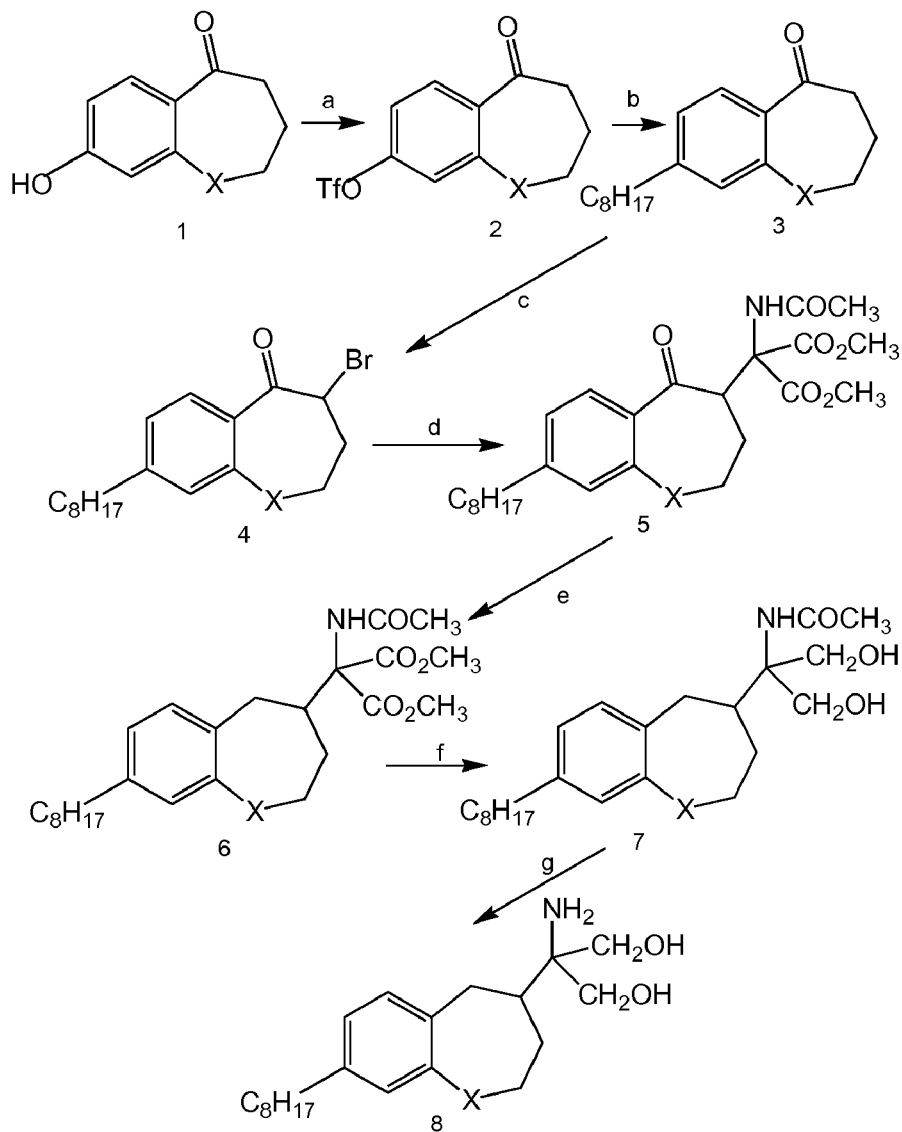

The following abbreviations are used herein: S1P, sphingosine-1-phosphate; $S1P_{1-5}$-S1P receptor types; GPCR, G-protein coupled receptor; SAR, structure-activity relationship; EDG, endothelial cell differentiation gene; EAE, experimental autoimmune encephalomyelitis; NOD non-obese diabetic; TNFα, tumor necrosis factor alpha; HDL, high density lipoprotein; and RT-PCR, reverse transcriptase polymerase chain reaction.

In describing and claiming the invention, unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. Each of the following terms has meaning associated with it in this section. Exemplary and preferred values listed below for radicals, substituents, and ranges are for illustrations only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "receptor agonists" are compounds that mimic the action of S1P at one or more of its receptors but may have differing potency and/or efficacy.

The term "receptor antagonists" are compounds that 1) lack intrinsic agonist activity and 2) block agonist (e.g., S1P) activation of the S1P receptor(s), often in a manner that is both fully surmountable and reversible ('competitive antagonist').

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound having the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. For example, an effective amount of an S1P receptor antagonist is an amount that decreases the cell signaling activity of the S1P receptor.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function. Preferably, inhibition is by at least 10%, more preferably by at least 25%, even more preferably by at least 50%, and most preferably, the function is inhibited by at least 75%.

"Instructional material" includes a publication, a recording, a diagram, or any other medium of expression which can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours, "rt" for room temperature, "THF" for tetrahydrofuran, and "rac" for racemic mixture).

The values listed below for radicals, substituents, and ranges, are for illustration only; they do not exclude other defined values or other values within defined ranges for the radicals and substituents. The disclosed compounds include compounds of Formula IA, IB, or IC having any combination of the exemplary values, preferred values, and more preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl or trifluoromethyl and the like. The term "$C_1$-$C_{20}$ alkyl" refers to a branched or linear alkyl group having from one to twenty carbons. Non-limiting examples include, but are not limited to, methyl, ethyl, n-propyl, iso-propyl, butyl, iso-butyl, sec-butyl, tert-butyl, pentyl, hexyl, heptyl, octyl and the like. The term "$C_2$-$C_{20}$ alkenyl", refers to an olefinically unsaturated branched or linear group having from two to twenty carbon atoms and at least one double bond. Typically, $C_2$-$C_{20}$ alkenyl groups include, but are not limited to, 1-propenyl, 2-propenyl, 1,3-butadienyl, 1-butenyl, hexenyl, pentenyl, hexenyl, heptenyl, octenyl and the like. The term ($C_2$-$C_{20}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like. The term "($C_1$-$C_{20}$) alkoxy" refers to an alkyl group attached through an oxygen atom. Examples of ($C_1$-$C_{10}$)alkoxy can be methoxy, ethoxy, propoxy, isopropoxy, butoxy, iso-butoxy, sec-butoxy, pentoxy, 3-pentoxy, hexyloxy, heptoxy, or octoxy and the like. The term ($C_2$-$C_{26}$)alkoxyalkyl can be methoxy methyl, methoxy ethyl, ethoxy methyl, ethoxy ethyl, and the like.

The term "$C_3$-$C_{12}$ cycloalkyl", can be cyclopropyl, cyclobutyl, cyclopentyl, cyclohexyl, cycloheptyl, cyclooctyl and the like.

The term "optionally substituted" refers to zero, one, two, three or four substituents, wherein the substituents are each independently selected. Each of the independently selected substituents may be the same or different than other substituents.

The term "($C_6$-$C_{10}$)aryl" refers to a mono or bicyclic carbocyclic ring system having one or two aromatic rings including, but not limited to, phenyl, benzyl, naphthyl, tetrahydronaphthyl, indanyl, indenyl, and the like.

The term "aryl($C_1$-$C_{20}$)alkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "optionally substituted aryl" includes aryl compounds having zero, one, two, three or four substituents, and a substituted aryl includes aryl compounds having one, two, three or four substituents, wherein the substituents include groups such as, for example, alkyl, halo, or amino substituents.

The "($C_2$-$C_{10}$)heterocyclic group" refers to an optionally substituted mono- or bicyclic carbocyclic ring system containing one, two, or three heteroatoms (optionally in each ring) wherein the heteroatoms are oxygen, sulfur, and nitrogen.

The term "($C_4$-$C_{10}$)heteroaryl" refers to an optionally substituted mono- or bicyclic carbocyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The term "bicyclic" represents either an unsaturated or saturated stable bridged or fused bicyclic carbon ring. The bicyclic ring may be attached at any carbon atom which affords a stable structure. Typically a bicyclic ring system can have from about 7- to about 12 atoms in the ring system. The term includes, but is not limited to, naphthyl, dicyclohexyl, dicyclohexenyl, and the like.

The term "phosphate analog" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, K, and the like if such counterions are present.

The term "alpha-substituted phosphonate" includes phosphonate (—$CH_2PO_3H_2$) groups that are substituted on the alpha-carbon such as —$CHFPO_3H_2$, —$CF_2PO_3H_2$, —$CHOHPO_3H_2$, —C=$OPO_3H_2$) and the like.

A "derivative" of a compound refers to a chemical compound that may be produced from another compound of similar structure in one or more steps, such as replacement of hydrogen by an alkyl, acyl, or amino group.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to salts which retain the biological effectiveness and properties of the disclosed compounds and which are not biologically or otherwise undesirable. In many cases, the disclosed compounds are capable of forming acid or base salts by virtue of the presence of amino or carboxyl groups or groups similar thereto.

An "effective amount" means an amount sufficient to produce a selected effect. For example, an effective amount of an S1P receptor agonist is an amount that decreases the cell signaling activity of the S1P receptor.

The disclosed compounds can contain one or more asymmetric centers in the molecule. In accordance with the present disclosure any structure that does not designate the stereochemistry is to be understood as embracing all the various optical isomers, as well as racemic mixtures thereof.

The disclosed compounds may exist in tautomeric forms and the invention includes both mixtures and separate individual tautomers. For example, the following structure:

is understood to represent a mixture of the structures:

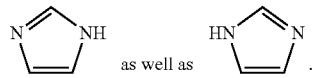

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

An "S1P modulating agent" refers to a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," refers to all of the S1P receptor subtypes (for example, the S1P receptors $S1P_1$, $S1P_2$, $S1P_3$, $S1P_4$, and $S1P_5$), unless the specific subtype is indicated.

The disclosed compounds can contain one or more asymmetric centers in the molecule. In accordance with the present disclosure any structure that does not designate the stereochemistry is to be understood as embracing all the various optical isomers, as well as racemic mixtures thereof.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof, of the compound, which possess the useful properties described herein, such as the S,R; S,S; R,R; or R,S diastereomers. It is well known in the art how to prepare such optically active forms (for example, resolution of the racemic form, recrystallization techniques, synthesis from optically-active starting materials, chiral synthesis, or chromatographic separation using a chiral stationary phase) and how to determine S1P agonist activity using the standard tests described herein, or using other similar tests which are well known in the art. In addition, some compounds may exhibit polymorphism.

Potential uses of an S1P receptor agonist pro-drugs ($S1P_1$ receptor type selective agonists preferred) include, but are not limited to, altering lymphocyte trafficking as a method of treatment for autoimmune pathologies such as uveitis, type I diabetes, rheumatoid arthritis, inflammatory bowel diseases, and, most particularly, multiple sclerosis. "Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

In addition, the disclosed compounds can be used for altering lymphocyte trafficking as a method for prolonging allograft survival, for example solid organ transplants, treatment of graft vs. host disease, bone marrow transplantation, and the like.

In addition, the disclosed compounds can be used to inhibit autotaxin. Autotaxin, a plasma phosphodiesterase, has been demonstrated to undergo end product inhibition. Autotaxin hydrolyzes several substrates to yield lysophosphatidic acid and sphingosine 1-phosphate, and has been implicated in cancer progression and angiogenesis. Therefore, S1P receptor agonist pro-drugs of the disclosed compounds can be used to inhibit autotaxin. This activity may be combined with agonism at S1P receptors or may be independent of such activity.

In addition, disclosed compounds can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, the disclosed compounds can be used to inhibit S1P lyase. This inhibition could be in concert with S1P receptor activity, or be independent of activity at any S1P receptor.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase(s) (MuLK). MuLK is highly expressed in many human tumor cells and thus its inhibition might slow the growth or spread of tumors.

"Treatment" of multiple sclerosis includes the various forms of the disease including relapsing-remitting, chronic progressive, etc., and the S1P receptor agonists can be used alone or in conjunction with other agents to relieve signs and symptoms of the disease as well as prophylactically.

In another aspect, the present invention provides compositions and methods for the use of the S1P analogs of the invention to prevent, inhibit, or treat neuropathic pain by agonizing or antagonizing the S1P receptors. Pain can be nociceptive or neuropathic in nature. Neuropathic pain is characterized by its chronic nature, an absence of an obvious, direct cause (i.e., tissue damage), and allodynia. Allodynia is the perception of normal stimuli as painful (examples include the touch of clothing, warm or cool air, etc.). Neuropathic pain is often a sequel to nerve damage in an extremity such as an arm, or more often, a leg. Typically, neuropathic pain is not responsive to opiates or non-steroidal anti-inflammatory drugs such as aspirin.

In another aspect, the present invention provides compositions and methods for the use of S1P analogs to prevent and inhibit vascular restenosis following vascular injury. In one aspect, the injury can be due to balloon angioplasty. The present invention further provides methods for treating subjects to prevent vascular restenosis.

In another aspect, the present invention provides compositions and methods for the use of sphingosine analogs (including S1P pro-drugs) to prevent asthma attacks. In one aspect, the asthma could be due to over production of cysteinyl leukotrienes. The present invention further provides methods for treating subjects to treat asthma.

In another aspect, the present invention provides compositions and methods for the use of sphingosine analogs (including S1P pro-drugs) to treat obesity.

In another aspect, the present invention provides compositions and methods for the use of sphingosine analogs (including S1P pro-drugs) to normalize blood lipid composition. In one aspect, blood low density lipoprotein (LDL or 'bad cholesterol') levels could be lowered. In another aspect, blood triglyceride levels could be lowered.

In another aspect, the present invention provides compositions and methods for the use of S1P analogs and S1P pro-drugs for the prevention and treatment of arteriosclerosis.

In another aspect, the present invention provides compositions and methods for the use of S1P analogs and S1P pro-drugs for the treatment of neoplastic disease. In one aspect, this treatment is effected by application of S1P receptor antagonists that are efficacious by virtue of their anti-angiogenic properties. In another aspect, the treatment is effected by administration of sphingosine analogs that inhibit the multiple substrate lipid kinase.

In another aspect, the present invention provides compositions and methods for the use of S1P analogs and S1P pro-drugs for the treatment of neurodegenerative diseases. In one aspect, the treatment is for senile dementia of the Alzheimers type.

The present invention also includes pharmaceutical compositions including the disclosed compounds. More particularly, such compounds can be Formulated as pharmaceutical compositions using standard pharmaceutically acceptable carriers, fillers, solubilizing agents and stabilizers known to those skilled in the art. For example, a pharmaceutical composition having a disclosed compound, or analog, derivative, or modification thereof, as described herein, is used to administer the appropriate compound to a subject.

The compounds of Formula IA, IB, or IC are useful for treating a disease or disorder including administering to a subject in need thereof of a therapeutically acceptable amount of a compound of Formula IA, IB, or IC, or a pharmaceutical composition including a therapeutically effective amount of a compound of Formula IA, IB, or IC, and a pharmaceutically-acceptable carrier.

The disclosed compounds and method are directed to sphingosine 1-phosphate (S1P) analogs that have activity as receptor agonists or antagonists at one or more S1P receptors, specifically the $S1P_1$, $S1P_4$ and $S1P_5$ receptor types. Disclosed compounds and method include both compounds that have a phosphate moiety as well as compounds with hydrolysis-resistant phosphate surrogates such as phosphonates, alpha-substituted phosphonates particularly where the alpha substitution is a halogen and phosphothionates.

Exemplary values listed below for radicals, substituents, and ranges, are for illustration only; they do not exclude other defined values or other values within defined ranges for the radicals and substituents.

Exemplary values for $W^1$, $X^1$, $Y^1$ and $Z^1$ are independently O, CH, $CH_2$, $CHCF_3$, N, NH, or S.

An additional exemplary value for $W^1$, $X^1$, $Y^1$ and $Z^1$ is $CH_2$.

Exemplary compounds have the Formula

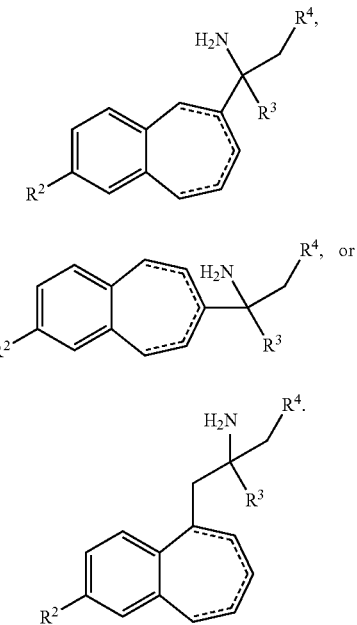

IXA

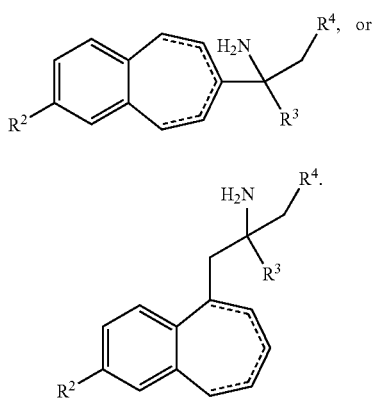

IXB

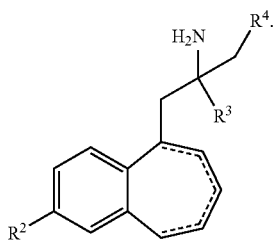

IXC

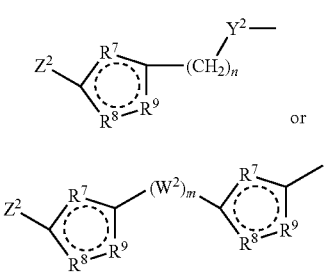

Exemplary values for $R^1$ include hydrogen, fluorine, chlorine, bromine, trifluoro-methyl, methoxy, $(C_1-C_6)$alkyl, $(C_1-C_6)$haloalkyl, or $(C_1-C_6)$alkyl substituted with, alkoxy or cyano.

More values for $R^1$ are hydrogen, trifluoro-methyl, or —$CH_2CF_3$.

Additional exemplary values for $R^1$ are alkyl-substituted aryl, aryl-substituted alkyl, or aryl-substituted arylalkyl.

Even more exemplary values for $R^1$ are benzyl, phenylethyl, or benzyl substituted with methyl.

Exemplary values for $R^2$ include

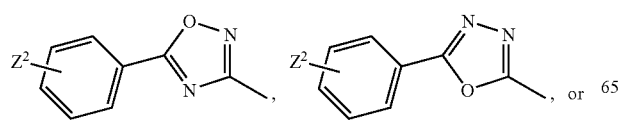

II or

III

An exemplary value for $W^2$ is a bond, —$CH_2$—$CH_2$—$CH_2$— or —$(C=O)(CH_2)_{1-5}$.

Additional values for $R^2$ having Formula VI are

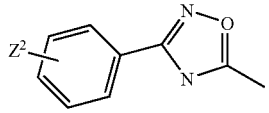

, or

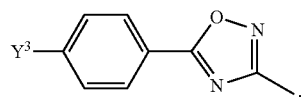

wherein $Z^2$ is $(CH_3)_3C$—, $CH_3CH_2(CH_3)_2C$—, $CH_3CH_2CH_2$—, $CH_3(CH_2)_2CH_2$—, $CH_3(CH_2)_4$—$CH_2$—, $(CH_3)_2CHCH_2$—, $(CH_3)_3CCH_2$—, $CH_3CH_2O$—, $(CH_3)_2CHO$—, or $CF_3CH_2CH_2$— or a group having the formula:

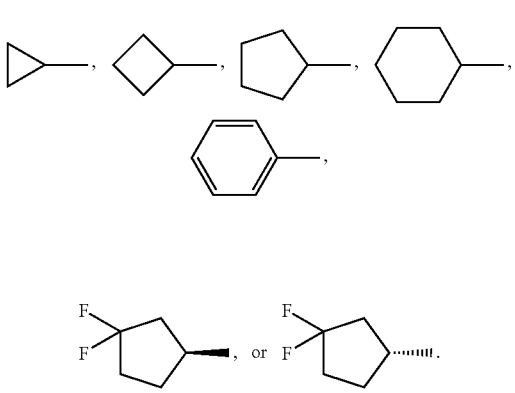

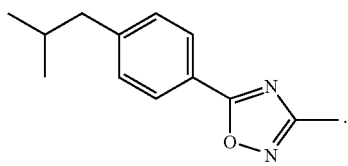

An additional value for an $R^2$ groups having Formula VI (sara substituted 3,5-diphenyl-(1,2,4)-oxadiazoles) is;

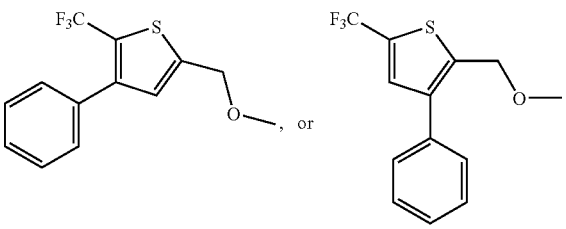

Another value for $R^2$ groups having Formula VI is;

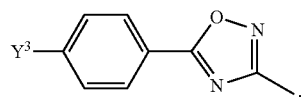

Additional values for $R^2$ groups having Formula II is;

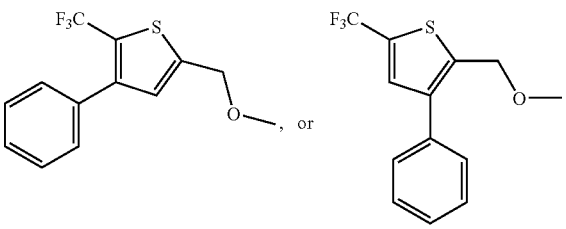

Another exemplary value for an $R^2$ group having Formula II is;

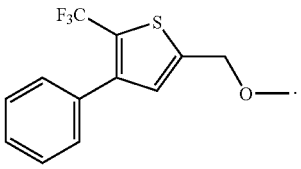

Additional values f for $R^2$ groups having Formula III are;

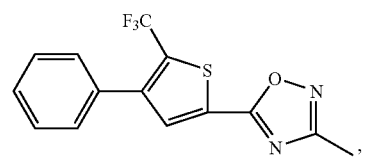

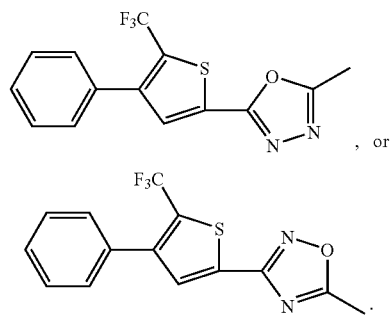

Another value for $R^2$ having formula V is;

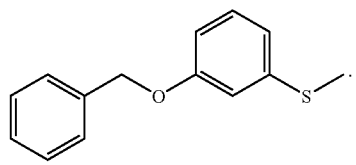

Additional exemplary values for $R^2$ include $(C_1-C_{20})$alkyl, $(C_1-C_{20})$alkoxy, or $(C_2-C_{26})$alkoxyalkyl.

More exemplary values for $R^2$ include $(C_1-C_{10})$alkyl, $(C_2-C_{10})$alkenyl and $(C_2-C_{14})$alkynyl or $(C_1-C_{10})$alkoxy optionally substituted with carbonyl (C=O) or oxime (C=NR$^d$) groups.

Additional values for $R^2$ include methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.

Exemplary values for $R^3$ include methyl, hydroxymethyl, ethyl, hydroxyethyl, propyl, hydroxypropyl, or isopropyl.

Additional values for $R^3$ include methyl, hydroxymethyl, ethyl, or hydroxyethyl.

Exemplary values for $R^4$ include is hydroxy, or phosphate (—OPO$_3$H$_2$).

Additional Embodiments

Additional embodiments of the invention include:
1. A compound of Formula IA, IB, or IC:

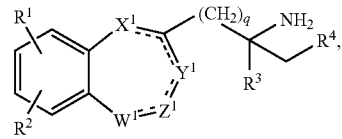
IA

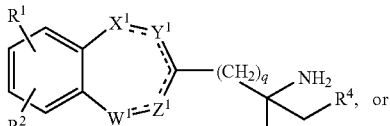
IB

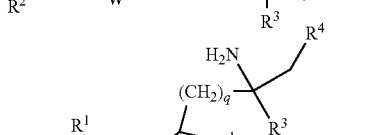
IC

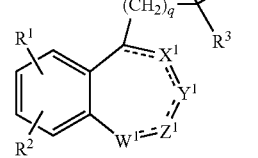

wherein $W^1$, $X^1$, $Y^1$ and $Z^1$ are independently O, CR$^a$, CR$^a$R$^b$, N, NR$^c$, or S;

$R^1$ and $R^2$ are independently hydrogen, halo, halo($C_1-C_{10}$)alkyl, cyano, —NR$^a$R$^b$, ($C_1-C_{20}$)alkyl, ($C_2-C_{20}$)alkynyl, ($C_1-C_{20}$)alkoxy, ($C_2-C_{26}$)alkoxyalkyl, ($C_3-C_{12}$)cycloalkyl, ($C_6-C_{10}$)aryl, ($C_7-C_{30}$)arylalkyl, ($C_2-C_{10}$)heterocyclic, ($C_4-C_{10}$)heteroaryl, or ($C_4-C_{10}$)heteroaryl ($C_1-C_{20}$)alkyl;

wherein the alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, ($C_1-C_{10}$)alkoxy, $C_6$-aryl, ($C_7-C_{24}$)arylalkyl, oxo (=O), or imino (=NR$^d$), wherein one or more of the carbon atoms in the $R^1$ or $R^2$ alkyl groups can be independently replaced with non-peroxide oxygen, sulfur or NR$^c$; the alkyl groups of $R^3$ are optionally substituted with 1, or 2 hydroxy groups; or $R^2$ can be a group having formula II, III, IV, V, or VI;

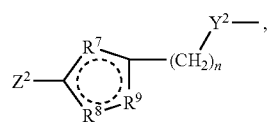
II

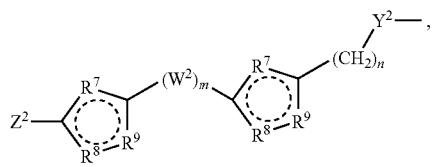
III

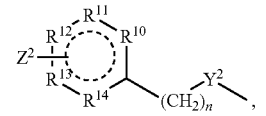
IV

-continued

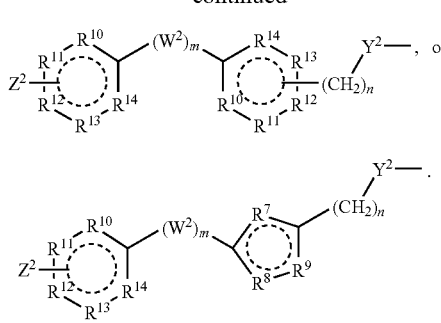

wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^{18}$;

each $R^{15}$, $R^{16}$ and $R^{17}$ is independently hydrogen, halo, $(C_1-C_{10})$alkyl, $(C_6-C_{10})$aryl, $(C_1-C_{10})$alkyl substituted with halo, hydroxy, $(C_1-C_{10})$alkoxy, or cyano; and where $R^{18}$ can be hydrogen or $(C_1-C_{10})$alkyl;

$Z^2$ is hydrogen, halo, halo$(C_1-C_{10})$alkyl, cyano, —$NR^aR^b$, $(C_1-C_{20})$alkyl, $(C_2-C_{20})$alkenyl, $(C_2-C_{20})$alkynyl, $(C_1-C_{20})$alkoxy, $(C_2-C_{26})$alkoxyalkyl, $(C_3-C_{12})$-cycloalkyl, $(C_6-C_{10})$aryl, $(C_7-C_{30})$arylalkyl, $(C_2-C_{10})$heterocyclic, $(C_4-C_{10})$heteroaryl, or $(C_4-C_{10})$heteroaryl$(C_1-C_{20})$alkyl;

the alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, $(C_1-C_{10})$alkoxy, $C_6$-aryl, $(C_7-C_{24})$arylalkyl, oxo (=O), or imino (=$NR^d$), wherein one or more of the carbon atoms in the $Z^2$ alkyl groups can be independently replaced with non-peroxide oxygen, sulfur or $NR^c$;

indicates one or more optional double bonds;

$Y^2$ is a bond (absent), O, S, C=O, or $NR^c$, $CH_2$; $W^2$ is a bond; —$CH_2$— and m is 1, 2, or 3, or $(C=O)(CH_2)_{1-5}$ and m is 1; wherein $W^2$ is optionally interrupted with non-peroxide O, S, C=O, or $NR^c$;

n is 0, 1, 2, or 3; each ---represents an optional double bond; and q is 0, 1, 2, or 3;

$R^3$ is hydrogen, $(C_1-C_{10})$alkyl, hydroxy$(C_1-C_{10})$alkyl or $(C_1-C_{10})$alkoxy; and $R^4$ is hydroxyl (—OH), phosphate (—$OPO_3H_2$), phosphonate (—$CH_2PO_3H_2$), alpha-substituted phosphonate;

each $R^a$, $R^b$, $R^c$, and $R^d$ is independently hydrogen, or $(C_1-C_{10})$alkyl; or a pharmaceutically acceptable salt or ester thereof.

2. The compound of embodiment 1, wherein $R^1$ is hydrogen, fluorine, chlorine, bromine, trifluoro-methyl, methoxy, $(C_1-C_6)$alkyl, $(C_1-C_6)$haloalkyl, $(C_1-C_6)$alkyl substituted with, alkoxy or cyano, alkyl-substituted aryl, aryl-substituted alkyl, or aryl-substituted arylalkyl.

3. The compound of embodiment 2, wherein $R^1$ is hydrogen, trifluoro-methyl, or —$CH_2CF_3$.

4. The compound of embodiment 2, wherein $R^1$ is benzyl, phenylethyl, or benzyl substituted with methyl.

5. The compound of any of embodiments 1-4, wherein $R^2$ is

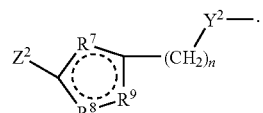

6. The compound of embodiment 5, wherein $R^2$ is:

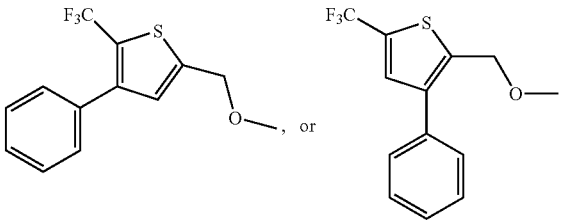

7. The compound of embodiment 6, wherein $R^2$ is

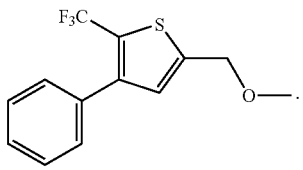

8. The compound of any of embodiments 1-4, wherein $R^2$ is:

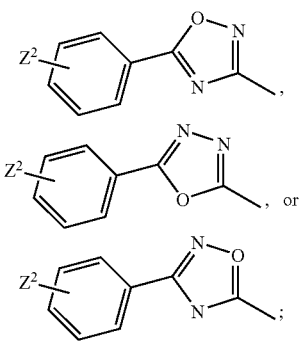

wherein $Z^2$ is $(CH_3)_3C$—, $CH_3CH_2(CH_3)_2C$—, $CH_3CH_2CH_2$—, $CH_3(CH_2)_2CH_2$—, $CH_3(CH_2)_4CH_2$—, $(CH_3)_2CHCH_2$—, $(CH_3)_3CCH_2$—, $CH_3CH_2O$—, $(CH_3)_2CHO$—, or $CF_3CH_2CH_2$— or a group having the formula:

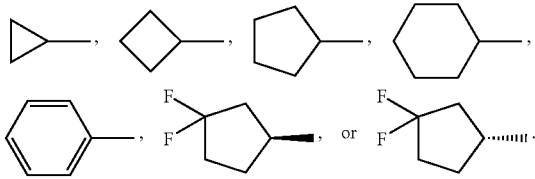

9. The compound of embodiment 8, wherein $R^2$ is:

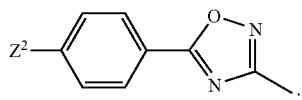

10. The compound of embodiment 9, wherein $R^2$ is:

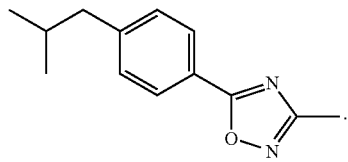

11. The compound of any of embodiments 1-4, wherein $R^2$ has Formula III

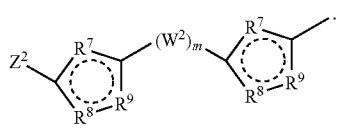

12. The compound of embodiment 11, wherein $R^2$ is

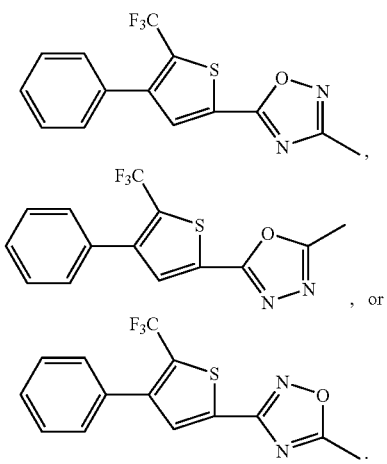

13. The compound of any of embodiments 1-4, wherein $R^2$ is $(C_1-C_{20})$alkyl, or $(C_1-C_{20})$alkoxy.
14. The compound of embodiment 13, wherein $R^2$ is $(C_1-C_{10})$alkyl, $(C_2-C_{10})$alkenyl and $(C_2-C_{14})$alkynyl or $(C_1-C_{10})$alkoxy optionally substituted with carbonyl (C=O) or oxime (C=NR$^d$) groups.
15. The compound of embodiment 14, wherein $R^2$ is methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.
16. The compound of any of embodiments 1-15, wherein each of $X^1$, $Y^1$ and $Z^1$ is $CH_2$.
17. The compound of any of embodiments 1-16, wherein $R^3$ is hydrogen, methyl, hydroxymethyl, ethyl, hydroxyethyl, propyl, or isopropyl.
18. The compound of embodiment 17, wherein $R^3$ is hydrogen, methyl, hydroxymethyl, ethyl, or hydroxyethyl.
19. The compound of any of embodiments 1-18, having the Formula

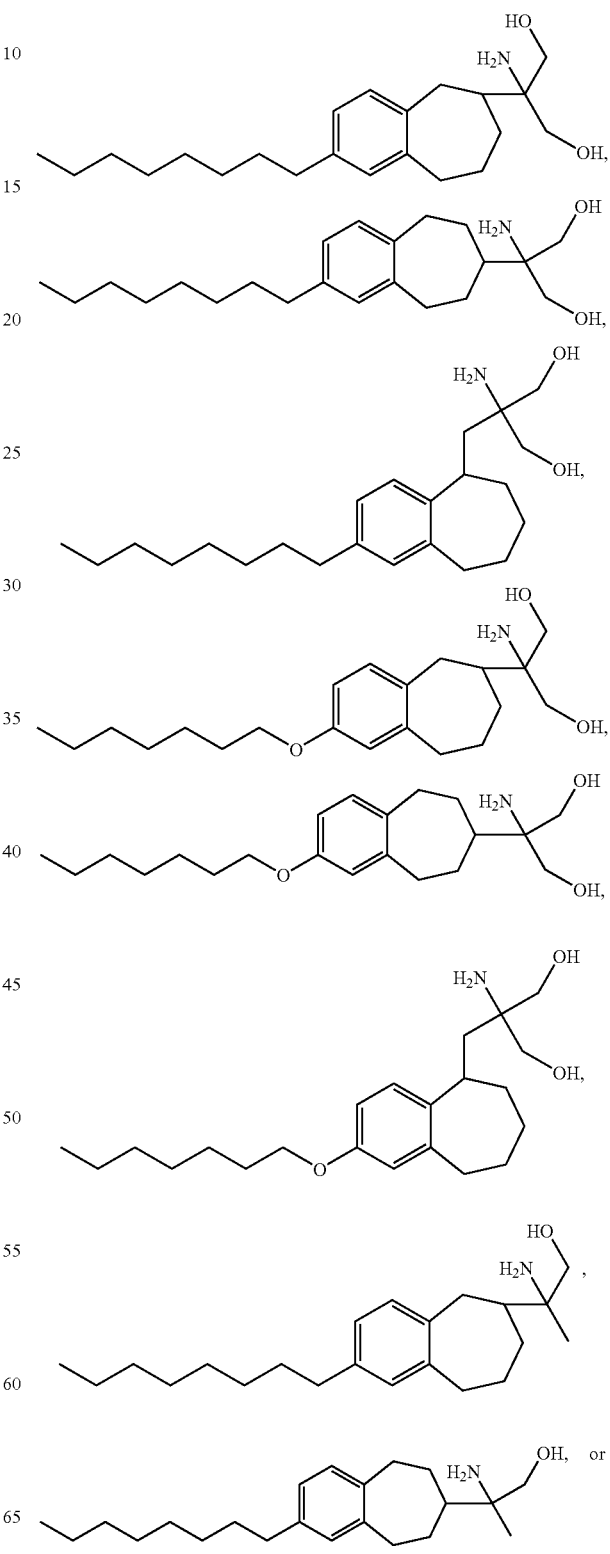

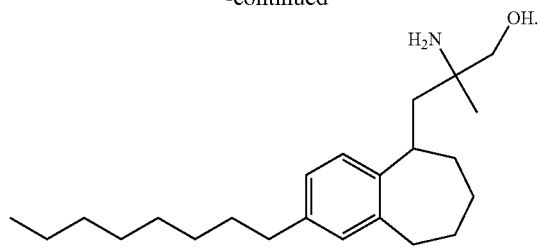

20. A method for prevention or treatment of a pathological condition or symptom in a mammal, wherein the activity of sphingosine 1-phosphate receptors is implicated and agonism of such activity is desired, comprising administering to said mammal an effective amount of a compound of any of embodiments 1-19.

21. The method of embodiment 20, wherein the pathological condition is an autoimmune disease.

22. The method of embodiment 21, wherein the autoimmune disease is uveitis, type 1 diabetes, rheumatoid arthritis, inflammatory bowel diseases, or multiple sclerosis.

23. The method of embodiment 22, wherein the autoimmune disease is multiple sclerosis.

24. The method of embodiment 23, wherein the pathological condition is altering lymphocyte trafficking.

25. The method of embodiment 24, wherein the treatment is altering of lymphocyte trafficking.

26. The method of embodiment 25, wherein lymphocyte trafficking provides prolonged allograft survival.

27. The method of embodiment 26, wherein the allograft is for transplantation.

28. A method for prevention or treatment of a pathological condition or symptom in a mammal, wherein the activity S1P lyase implicated and inhibition of the S1P lyase is desired, comprising administering to said mammal an effective amount of a compound of any of embodiments 1-19.

29. A compound of any of embodiments 1-19, for use in medical therapy.

30. Use of a compound of any of embodiments 1-19, to prepare a medicament useful for prevention or treatment of a pathological condition or symptom in a mammal, wherein the activity of sphingosine 1-phosphate receptors is implicated.

31. The use of embodiment 30, wherein the medicament comprises a carrier.

32. The use of embodiment 31, wherein the carrier is a liquid.

Exemplary compounds of the invention have Formulas

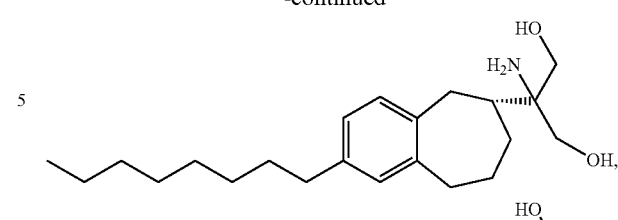
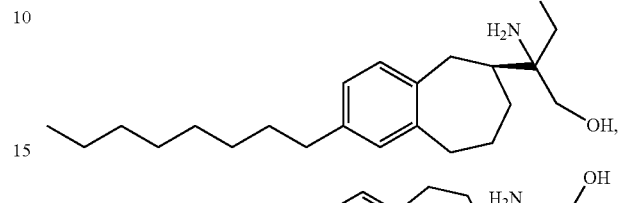
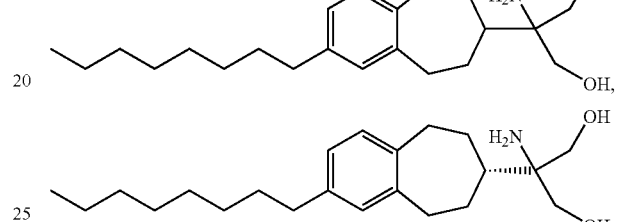
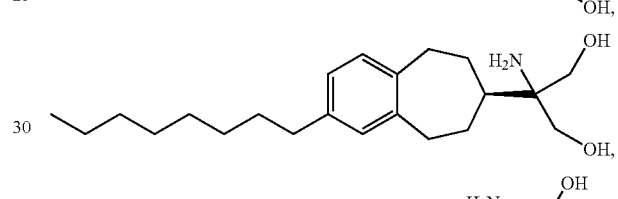
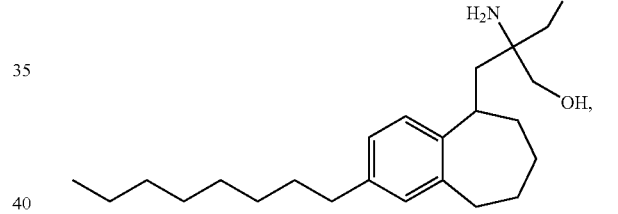
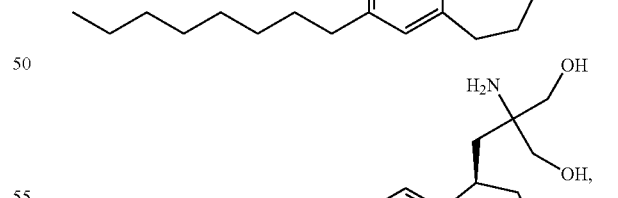
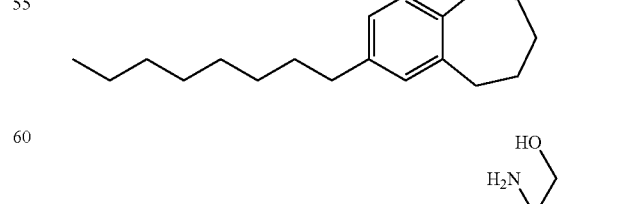
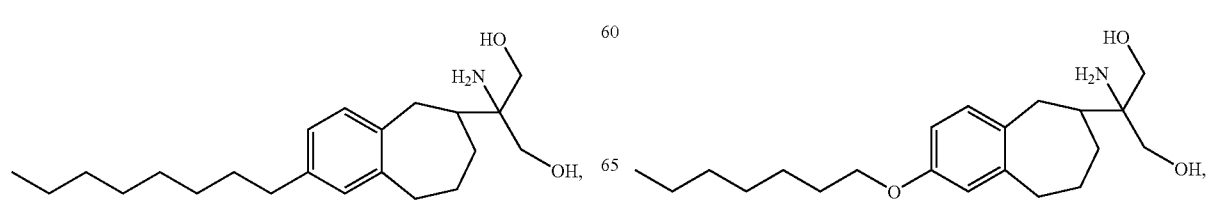

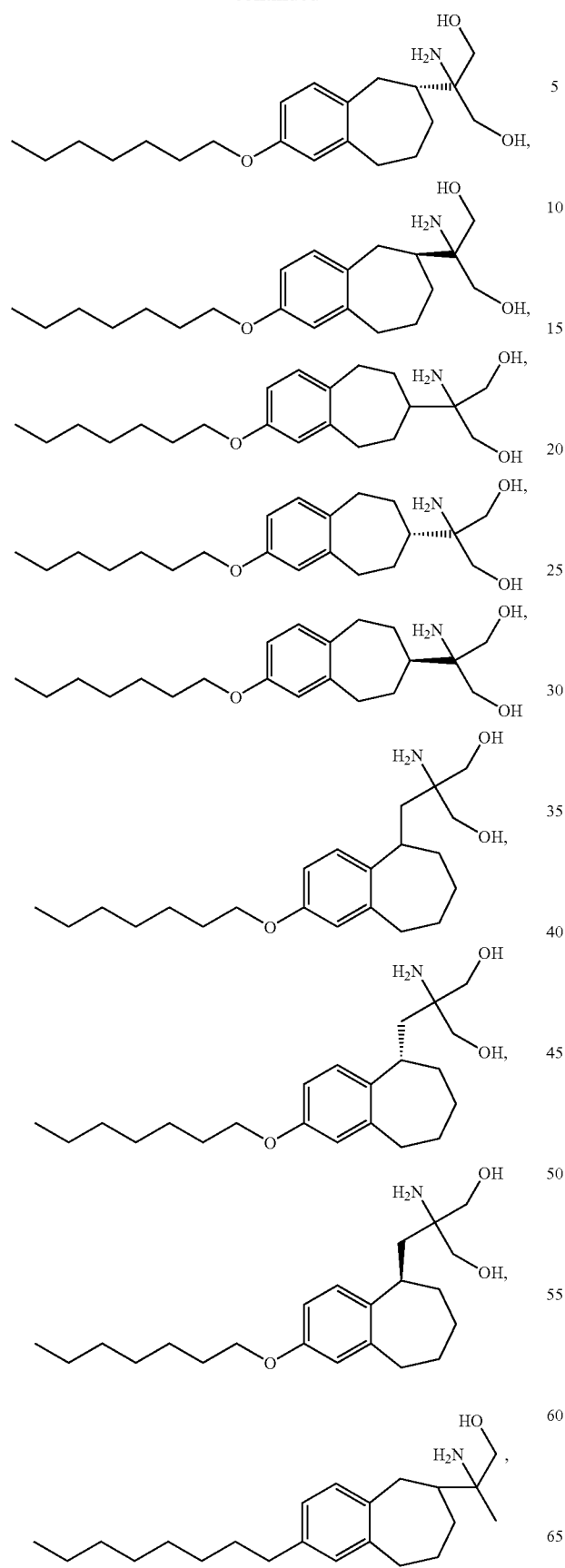
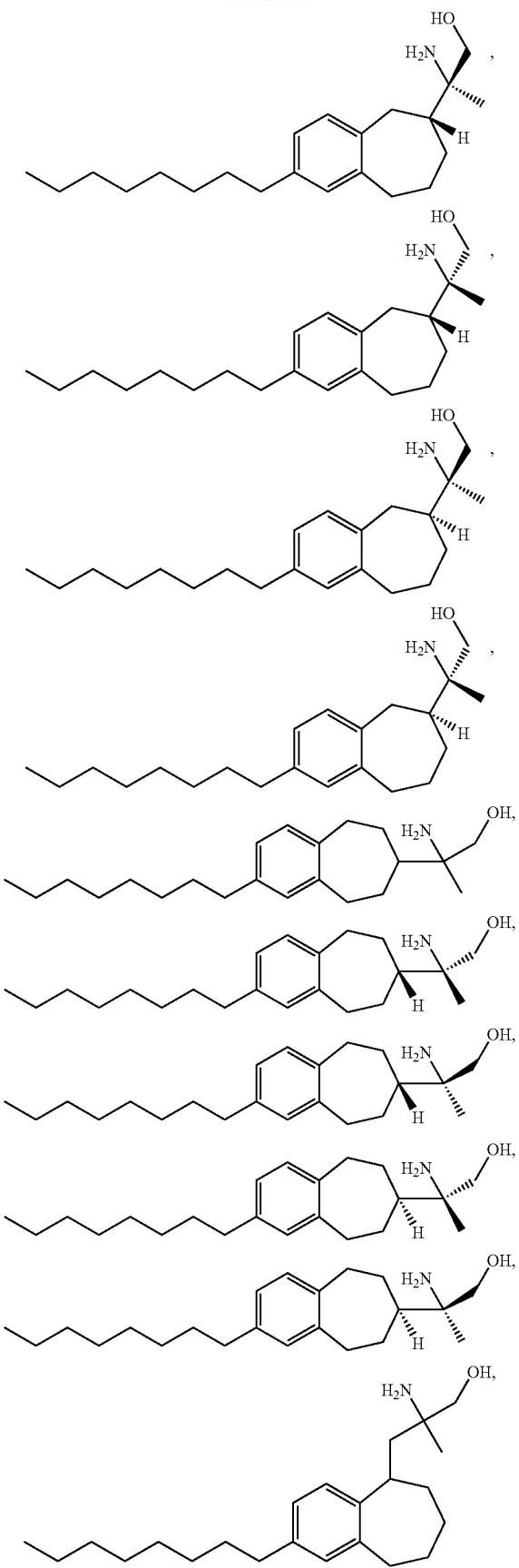

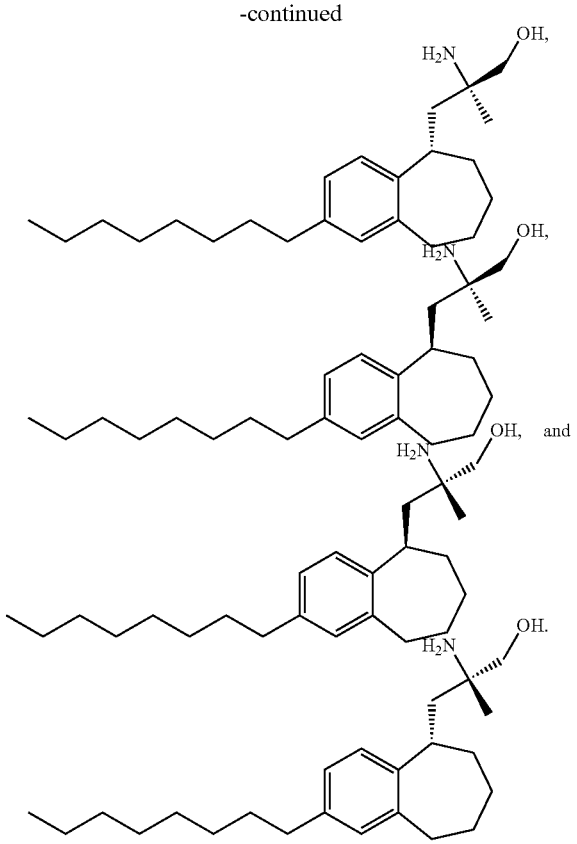
Additional exemplary compounds are illustrated in FIG. 1. Additional compounds of Formula IA, IB, or IC are illustrated in table 1, below.

The compounds having formulas XX through XXV or XXXI also include all enantiomers thereof such as:

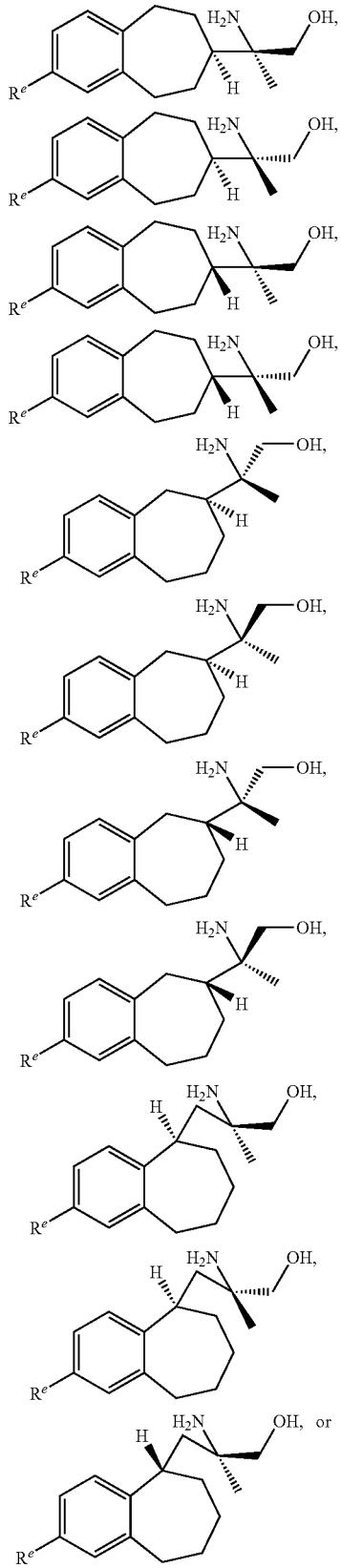

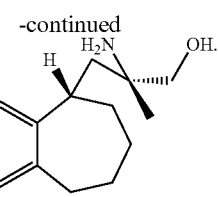

where the compounds include each of the $R^e$ groups from Table 1.

In another aspect, S1P receptor pro-drug compounds having the general structure of Formula IA, IB, or IC, are provided by compounds with a mono-substituted ring system having structure (VIII). In some embodiments of structure (I), the compound (e.g., IX) may have only a single chiral center and that the amino carbon is pro-chiral, i.e., will become chiral following enzyme-catalyzed phosphorylation.

Without wishing to be bound by any particular theory, it is expected that the compounds described herein are pro-drugs, e.g. are activated by phosphorylation of the primary alcohol to form the mono-phosphorylated analog. Additionally, the active drugs are expected to be agonists at the S1P type 1 receptor.

In cases where compounds of Formula IA, IB, or IC are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of Formula IA, IB, or IC can be Formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders having the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or Formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula IA, IB, or IC to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of Formula IA, IB, or IC can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of Formula IA, IB, or IC in a liquid composition, such as a lotion, will be from about 0.1 to about 25 weight percent, preferably from about 0.5-10 weight percent. The concentration in a semi-solid or solid composition such as a gel or a powder will be about 0.1-5 weight percent preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit including an inhibitor compound of Formula IA, IB, or IC and instructional material that describes administering the inhibitor compound or a composition including the inhibitor compound to a cell or a subject. This should be construed to include other embodiments of kits that are known to those skilled in the art, such as a kit having a (preferably sterile) solvent for dissolving or suspending the inhibitor compound or composition prior to administering the compound or composition to a cell or a subject. Preferably, the subject is a human.

The disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the disclosed compounds.

Processes for preparing compounds of Formula IA, IB, or IC or for preparing intermediates useful for preparing compounds of Formula IA, IB, or IC are provided as further embodiments. Intermediates useful for preparing compounds of Formula IA, IB, or IC are also provided as further embodiments. The processes are provided as further embodiments and are illustrated in the schemes herein wherein the meanings of the generic radicals are as given above unless otherwise qualified.

Processes for preparing compounds of Formula IA, IB, or IC or for preparing intermediates useful for preparing compounds of Formula IA, IB, or IC are provided as further embodiments of the invention. Intermediates useful for preparing compounds of Formula IA, IB, or IC are also provided as further embodiments of the invention. The compounds of the invention can be prepared using starting materials and methods known in the art.

The syntheses of target molecules are illustrated in Scheme 1, Scheme 2, and Scheme 3 (See FIGS. 3-6).

The invention is now described with reference to the following Examples and Embodiments. Without further description, it is believed that one of ordinary skill in the art can, using the preceding description and the following illustrative examples, make and utilize the disclosed compounds. The following working examples therefore, are provided for the purpose of illustration only, point out the preferred embodiments, and are not to be construed as limiting in any way the remainder of the disclosure. Therefore, the examples should be construed to encompass any and all variations which become evident as a result of the teaching provided herein.

EXAMPLES

Example 1

Trifluoro-methanesulfonic acid 6,7,8,9-tetrahydro-5H-benzocyclohepten-5-on-2-yl ester (2)

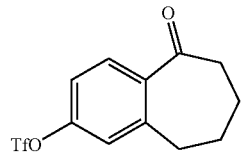

Trifluoromethanesulfonic anhydride (1.7 mL, 10 mmol) was added slowly over 1 h to a solution of 7-hydroxy-1-benzosuberone (2-hydroxy-6,7,8,9-tetrahydro-5H-benzocyclohepten-5-one, 1.75 g, 10 mmol) and 2,6-lutidine (1.28 mL, 10 mmol) in dry dichloromethane (10 mL) cooled to 0° C. After 1 h. the solution was diluted with dichloromethane (10 mL) and washed with 1 M hydrochloric acid (20 mL). The organic layer was re-extracted with dichloromethane (50 mL) and the combined organics washed with 1 M hydrochloric acid (10 mL). The organics were then dried over magnesium sulfate and concentrated under vacuum. The residue was purified by column chromatography (Silica gel, $CH_2Cl_2$) to give 2.7 g compound 2 (90%). $^1$H NMR (300 MHz, $CDCl_3$) δ 2.13 (m, 4H, J=6.22 Hz), 2.63 (t, 2H, J=6.95 Hz), 2.98 (t, 2H, J=6.22 Hz), 7.15 (m, 2H), 8.07 (m, 1H.

Example 2

2-Octyl-6,7,8,9-tetrahydro-5H-benzocyclohepten-5-one (3)

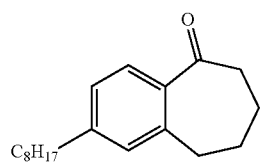

(7-octyl-1-benzosuberone). 9-BBN (0.5 M solution in THF, 20.2 mL, 10.1 mmol) was added to 1-octene (1.6 mL, 10.1 mmol) at rt. The solution was then stirred at room temperature overnight. After this time, K₃PO₄ (2.93 g, 13.8 mmol), Pd(Ph₃P)₄ (191 mg, 0.17 mmol, 1.8 mol %), KBr (1.2 g, 10.1 mmol) and degassed H₂O (0.18 mL, 10 mmol) were added followed by a solution of 2 (2.7 g, 9.2 mmol) in dry degassed THF (10 mL). The reaction mixture was then heated to 65° C. under argon for 2 h. After cooling the solution was acidified to pH 1 and extracted into EtOAc (100 mL). The aqueous layer was re-extracted with EtOAc (50 mL) and the combined organics washed with H₂O (20 mL) and brine (40 mL). The organic layer was dried over magnesium sulfate and concentrated under vacuum. The residue was purified by column chromatography (Silica gel, 5% EtOAc in hexanes) to give 1.45 g compound 3 (72%). ¹H NMR (300 MHz, CDCl₃) δ 0.85 (t, 3H, J=6.95 Hz), 1.24 (bs, 10H), 1.58 (p, 2H, J=6.95 Hz), 2.06 (m, 4H, J=5.85 Hz), 2.57 (t, 4H, J=6.95 Hz), 2.87 (t, 2H, J=6.22 Hz), 7.01 (s, 1H), 7.06 (d, 1H, J=8.05 Hz), 7.91 (d, 1H, J=8.06 Hz).

Example 3

6-Bromo-2-octyl-6,7,8,9-tetrahydro-5H-benzocyclohepten-5-one (4)

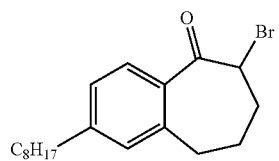

4

(2-bromo-7-octyl-1-benzosuberone). Cupric bromide (3.34 g, 15.0 mmol,) was heated at reflux in ethyl acetate (10 mL) with stirring. To this was added compound 3 (1.93 g, 7.5 mmol) in chloroform (10 mL). The reaction was heated at reflux for a further 6 h and then cooled. Copper bromide and cupric bromide residues were filtered off and the filtrate was decolourised with activated charcoal and filtered through a bed of Celite and washed with ethyl acetate (4×50 mL). The solvent was removed under reduced pressure and the residue was purified by column chromatography (Silica gel, 2% EtOAc in hexanes) to give 2.02 g compound 4 (80%). ¹H NMR (300 MHz, CDCl₃) δ 0.87 (t, 3H, J=6.95 Hz), 1.26 (bs, 10H), 1.61 (p, 2H, J=6.96 Hz), 2.46 (m, 2H), 2.62 (t, 2H, J=7.69 Hz), 2.86 (dt, 1H, J=16.34 Hz, 4.39 Hz), 3.27 (dt, 1H, J=16.83 Hz, 4.39 Hz), 4.69 (t, 1H, J=4.02 Hz), 7.07 (s, 1H), 7.14 (d, 1H, J=8.05 Hz), 7.99 (d, 1H, J=8.05 Hz); ¹³C NMR δ 14.34, 22.88, 26.42, 29.44, 29.57, 29.64, 31.25, 32.08, 32.32, 36.39, 127.75, 128.00, 128.73, 129.00, 144.30, 150.39, 190.54.

Example 4

2-Acetylamino-2-(2-octyl-6,7,8,9-tetrahydro-5H-benzocyclohepten-5-on-6-yl)-malonic acid dimethyl ester (5)

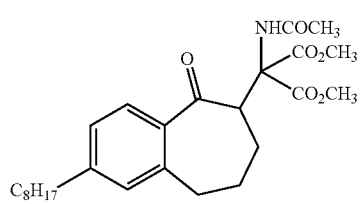

5

Sodium hydride (720 mg, 18.0 mmol) 60% in mineral oil was suspended in dry DMF (10 mL) and a solution of dimethyl acetamidomalonate (3.00 g, 15 mmol) in dry DMF (10 mL) was added. The solution was stirred at 0° C. for 3 h until the anion had formed. A solution of 4 (2.12 g, 6.0 mmol) in dry DMF (10 mL) was added and the solution warmed to room temperature and stirred overnight. The mixture was poured into distilled water (50 mL), acidified to pH 3 with 1M hydrochloric acid in an ice-bath and extracted into ethyl acetate (3×50 mL). The organic phases were washed with brine (2×30 mL) and dried over magnesium sulfate and concentrated under vacuum. The residue was purified by column chromatography (Silica gel, 40% EtOAc in hexanes) to give 0.420 g compound 5 (15%). ¹H NMR (300 MHz, CDCl₃) δ 0.85 (t, 3H, J=6.22 Hz), 1.24 (m, 10H), 1.58 (p, 2H, J=6.95 Hz), 1.97 (s, 3H), 2.45-2.60 (m, 4H), 2.83-3.21 (m, 4H), 3.88 (dd, 1H, J=14.00 Hz, 3.68 Hz), 4.05 (s, 6H), 6.86 (s, 1H), 7.03 (s, 1H), 7.07 (d, 1H, J=8.69 Hz), 7.84 (d, 1H, J=8.36 Hz).

Example 5

2-Acetylamino-2-(2-octyl-6,7,8,9-tetrahydro-5H-benzocycloheptenyl)-malonic acid dimethyl ester (5)

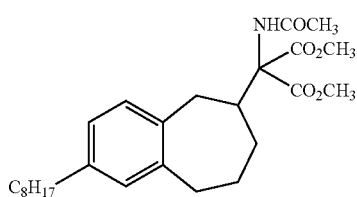

6

To a solution of triethylsilane (1.3 ml, 8.2 mmol) in 5 ml of CH₂Cl₂ was added compound 5 (1 g, 2.1 mmol) in 5 ml of CH₂Cl₂. The reaction mixture was stirred at room temperature under Ar and TiCl₄ (0.09 ml, 8.2 mmol) was added dropwise. The resulting solution was stirred for 12 h, cooled to 0° C. and quenched with 10 ml of saturated NaHCO₃ by slow addition. The aqueous layer was extracted with CH₂Cl₂ (3×30 mL). The combined organic layers were washed with brine (2×30 mL) and dried over magnesium sulfate and concentrated under vacuum. The residue was purified by column chromatography (Silica gel, 20% EtOAc in hexanes) to give 570 mg compound 6 (55%). ¹H NMR (300 MHz, CDCl₃) δ 0.87 (t, 3H, J=6.46 Hz), 1.26 (m, 10H), 1.58 (p, 2H, J=6.79 Hz), 2.03 (s, 3H), 2.28 (b, 1H), 2.30-2.68 (m, 6H), 2.82-2.92 (m, 2H), 4.05 (s, 6H), 6.69 (s, 1H), 6.89-7.05 (m, 3H).

Example 6

N-[2-Hydroxy-1-hydroxymethyl-1-(2-octyl-6,7,8,9-tetrahydro-5H-benzocyclohepten-6-yl)-ethyl]-acetamide (7)

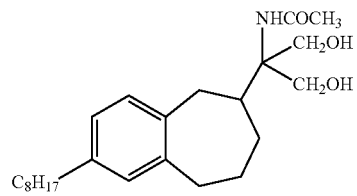

7

Lithium borohydride (2M solution in THF, 0.88 ml, 1.76 mmol) was added to compound 6 (200 mg, 0.44 mmol) in 5 ml THF at 0° C. The reaction mixture was stirred at room temperature for 48 h and then diluted with 40 ml ethyl acetate.

The solution was washed with brine (2×20 mL) and dried over magnesium sulfate and concentrated under vacuum. The residue was purified by column chromatography (Silica gel, 4% MeOH in $CH_2Cl_2$) to give 59 mg compound 7 (33%). $^1$H NMR (300 MHz, $CDCl_3$) δ 0.88 (t, 3H, J=6.56 Hz), 1.29 (m, 10H), 1.57 (p, 2H, J=6.25 Hz), 1.94-1.98 (m, 2H), 2.05 (s, 3H), 2.20-2.45 (m, 3H), 2.51 (t, 2H, J=7.32), 2.60-2.85 (m, 4H), 3.69 (d, 2H, J=11.61), 3.89 (dd, 2H, J=11.61 Hz, 7.25 Hz), 6.22 (s, 1H), 6.88-6.99 (m, 3H).

Example 7

2-Amino-2-(-(2-octyl-6,7,8,9-tetrahydro-5H-benzo-cyclohepten-6-yl)-propane-1,3-diol 8

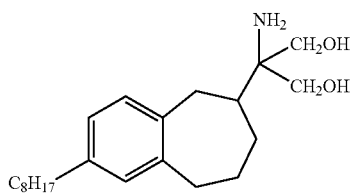

A solution of compound 7 (55 mg, 0.14 mmol) and $LiOH \cdot H_2O$ (45 mg, 1.1 mmol) in MeOH (3 ml), THF (1.5 ml) and water (3 ml) was stirred at 50° C. for 5 h and then diluted with ethyl acetate (20 ml). The solution was washed with brine (2×10 mL) and dried over magnesium sulfate and concentrated under vacuum. The residue was purified by column chromatography (Silica gel, 50% MeOH in $CH_2Cl_2$) to give 35 mg compound 8 (75%). $^1$H NMR (300 MHz, $CDCl_3$) δ 0.88 (t, 3H, J=6.17 Hz), 1.29 (m, 10H), 1.56 (p, 2H, J=6.17 Hz), 1.82-2.05 (m, 4H), 2.51 (t, 2H, J=6.95), 2.58-2.88 (m, 5H), 3.19 (b, 4H), 3.61 (d, 2H, J=10.98), 3.73 (d, 2H, J=10.61 Hz), 6.87-6.98 (m, 3H).

Example 8

Compound 9

The ylide of 1-[5-(O-tetrahydropyranyl)butyloxy]triph-enylphosphonium bromide (8.38 g. 20.0 mmol) is generated in THF (150 mL) in situ by the addition of s-butyl lithium (22.0 ml of 1.1 M solution in hexane, 22.0 mmol) at −40° C. The reaction is allowed to warm to 0° C. and stirred for 1 hour under an inert atmosphere before returning to −40° C. and adding 3-bromobenzaldehyde (3.68 g, 20.0 mmol) in THF (50 mL) dropwise. The reaction is maintained at −40° C. for 1 hour, then brought to room temperature and maintained for 4 hours. The reaction is partitioned between ether (200 mL) and water (100 mL) and the organic layer is separated, washed with aqueous sodium bicarbonate (5% w/w, 100 mL) and dried over sodium sulfate. The organic layer is evaporated in vacuo. The product is purified using silica gel chromatography with hexanes (85%)-ethyl acetate (15%) and usually provides a mixture of E- and Z-alkene diastereomers.

Example 9

Compound 10

An octyl boronate intermediate is generated in situ by adding 1-octene (1.38 g, 14.1 mmol) to a solution of 9-BBN in THF (28.3 mL of a 0.5 M solution, 14.1 mmol).

The reaction is stirred at room temperature overnight, then an aqueous solution of sodium hydroxide (5.0 mL of a 3.0 M solution) is added, followed by the addition of compound 9 (3.25 g, 10.0 mmol) and $Pd[P(Ph)_3]_4$ (0.310 g, 0.270 mmol). The reaction is brought to reflux and maintained for 12 hours under an inert atmosphere. The reaction is cooled, filtered, and concentrated in vacuo. The residue is purified using silica gel chromatography with hexane/ethyl acetate (85:15) as solvent. The purified compound 10 is usually obtained as a mixture of E- and Z-alkene diastereomers.

Example 10

Compound 11

Chlorine (0.700 g, 1.0 mmol) is condensed in methylene chloride (100 mL) maintained at −40° C. and compound 10 (3.22 g, 9.0 mmol) in methylene chloride (25 mL) is added dropwise. The reaction is allowed to warm to 0° C. and stirred for 1 hour. The reaction is then quenched by the addition of aqueous sodium bicarbonate (5% w/w, 100 mL), the organic layer separated and the aqueous phase extracted with ether (100 mL). The combined organic layers are dried over sodium sulfate and the solvents removed in vacuo. The residue is purified by silica gel chromatography using hexanes (85%)-ethyl acetate (15%) to furnish compound 11.

Example 11

Compound 12

Compound 11 (2.90 g, 6.75 mmol) is dissolved in isopropanol (100 mL) and aqueous sulfuric acid (10 mL of a 5.0 N solution) is added. The reaction is stirred overnight at room temperature under an inert atmosphere, then ether (100 mL) and water (100 mL) are added and the organic layer separated. The aqueous phase is extracted with ether (2×50 mL) and the combined organic layers are washed with aqueous sodium bicarbonate (5% w/w, 2×100 mL) and dried over sodium sulfate. The organic layer is evaporated in vacuo to give an oil, that is used in the next reaction without purification.

Example 12

Compound 13

Compound 12 (~2.33 g, ~6.75 mmol) is dissolved in acetone (100 mL) at 0° C. and Jones reagent is added dropwise slowly until the reagent color is maintained. Ethanol is then added to quench excess Jones reagent and the mixture partitioned between ether (200 mL) and water (100 mL). The aqueous layer is extracted with ether (2×100 mL) and the combined organic layers are washed with water (1×100 mL) and dried over sodium sulfate. The solvents are removed in vacuo to give an oil that can be purified using silica gel chromatography with ethyl acetate (30%)-hexanes (70%) to give compound 13.

Example 13

Compound 14

Compound 13 (1.93 g, 5.4 mmol) is added to polyphosphoric acid (100 mL) and the mixture heated to 80° C. under an inert atmosphere for 2 hours. The mixture is cooled and carefully decanted into an ice water (200 mL)/methylene chloride (100 mL) two phase solution. The organic layer is separated and the aqueous phase extracted with methylene chloride (2×50 mL). The combined organic layers are washed with aqueous sodium bicarbonate (5% w/w, 2×100 mL), dried over MgSO$_4$ and the solvents removed in vacuo. The residue is purified by silica gel chromatography using hexanes (90%)-ethyl acetate (10%) to furnish the benzosuberone compound 14.

Example 14

Compound 15

Compound 14 (1.11 g, 3.25 mmol) in chloroform (5.0 mL) is added dropwise to a mixture of refluxing cupric bromide (1.5 g, 6.68 mmol) in ethyl acetate (5.0 mL). The reaction is heated for an additional 6 hours, then cooled and filtered through Celite. The Celite is washed with additional ethyl acetate (4×50 mL) and the combined organic layers are dried over MgSO$_4$ and the solvents removed in vacuo. The residue can be purified on silica gel chromatography using hexanes (95%)-ethyl acetate (5%) to furnish compound 15.

Example 15

Compound 16

Sodium hydride (360 mg, 9.0 mmol) as a 60% suspension in mineral oil is added to dry dimethyl formamide (5 mL) and a solution of dimethyl acetamidomalonate (1.50 g, 7.5 mmol) in dry dimethyl formamide (5 mL) is added. The solution is stirred at 0° C. for 3 hours to enable anion formation, a solution of compound 7 (1.10 g, 2.60 mmol) in dry DMF (5 mL) added and the solution warmed to room temperature and stirred overnight. The mixture is poured into water (25 mL), acidified to pH 3 with 1M aqueous hydrochloric acid in an ice bath and extracted into ethyl acetate (4×25 mL). The combined organic phases are washed with brine (25 mL), dried over MgSO$_4$ and the solvents removed in vacuo. The residue can be purified using silica gel chromatography with ethyl acetate (5%)-hexanes (95%) to furnish compound 16.

Example 16

Compound 17

Compound 16 (130 mg, 0.25 mmol) is added to a solution of triethylsilane (0.125 mL, 0.85 mmol) in methylene chloride (2.0 mL) at room temperature. Titanium tetrachloride (0.01 mL, 0.85 mmol) is added dropwise and the resulting solution stirred for 12 hours. The reaction is cooled to 0° C. and quenched with aqueous sodium bicarbonate solution (5% w/w. 4 mL) by slow addition. The organic layer is removed and the aqueous phase extracted with methylene chloride (2×5 mL), dried over magnesium chloride and concentrated in vacuo. The residue can be purified by silica gel chromatography with ethyl acetate (15%)-hexanes (85%) to afford compound 17 (88 mg, 0.18 mmol, 70%).

Example 17

Compound 18

A small magnesium shaving (~5 mg) is placed in anhydrous THF (5 mL) at 0° C. and activated with ethylene dibromide (1 drop). Compound 17 (88 mg, 0.18 mmol) dissolved in THF (2 mL) is added dropwise and the reaction allowed to warm to room temperature. The reaction is stirred vigorously for 2 hours at room temperature, and partitioned between ether (10 mL) and ice water (10 mL). The water layer is extracted with ether (10 mL) and the combined organic layer dried over MgSO$_4$ and the solvents removed in vacuo. The residue is used the next reaction without purification.

Example 18

Compound 19

Lithium borohydride (2 M solution in THF, 0.44 mL, 0.88 mmol) is added to compound 18 prepared in Example 16 (~90 mg, ~0.20 mmol) in THF (5.0 mL) at 0° C. The reaction mixture is stirred at room temperature for 48 hours and then diluted with ethyl acetate (10 mL). The solution is washed with water (5 mL), then brine (5 mL) and dried over MgSO$_4$ and concentrated in vacuo. The residue could be purified by silica gel chromatography using methanol (5%)-methylene chloride (95%) to afford compound 19.

Example 19

Compound 20

Compound 19 (28 mg, 0.075 mmol) is dissolved a solution of methanol (3 mL), THF (1 mL) and water (2 mL) containing lithium hydroxide (45 mg, 1.1 mol). The reaction is heated to 50° C. for 5 hours then partitioned between ethyl acetate (10 mL) and water (5 mL). The aqueous phase is extracted with methylene chloride (2×5 mL) and the combined organic layers and dried over sodium sulfate, then concentrated under vacuum. The residue can be purified on silica gel chromatography to furnish compound 20.

The assays below are standard literature reported assays known in the art for confirming and quantifying the activity of the disclosed compounds.

Example 20

Sphingosine Kinase Assay

Recombinant sphingosine kinase type 2 (SPHK2) is prepared by forcing the expression of the mouse or human recombinant enzyme by transfecting the relevant plasmid DNA into HEK293T or CHO K1 cells. After about 60 hours, cells are harvested, broken and the non-microsomal (e.g., soluble) fraction is retained. The broken cell supernatant fluid containing the recombinant enzyme is mixed with test compounds (e.g., FTY720, AA151, VIII and XVIII) (5-50 micromolar) and γ-32P-ATP and incubated for 0.5-2.0 hours at 37° C. The lipids in the reaction mixture are extracted into an organic solvent and displayed by normal phase thin layer chromatography. The radio-labeled bands are detected by autoradiography, scraped from the plate and quantified by scintillation counting. The test compounds are used at a concentration of about 50 μM, incubation time is about 20 minutes.

Example 21

GTPγS-35 Binding Assay

This assay illustrates agonist activation of G protein coupled receptors (GPCRs) in isolation. The assay forces expression concomitantly of a recombinant GPCR (e.g., the S1P1-5 receptor) and each of the three subunits (e.g., α-i2, β-1, and γ-2) of a heterotrimeric G protein in a HEK293T cell by transfecting the cell with four plasmid DNAs encoding the respective proteins. About 60 hours after transfection cells are harvested, broken, the nucleus discarded, and the crude microsomes are prepared from the remainder. Agonist (e.g., S1P) stimulation of the receptor-G protein complex on the microsomes results in the exchange of GTP for GDP on the α-subunit in a dose-dependent manner. The GTP-bound α-subunit is detected using a GTP analog (GTPγS-35), which is a radionuclide (sulfur-35) labeled phosphothionate that is not hydrolyzed to GDP. The microsomes with the adherent G proteins are collected by filtration and the bound GTPγS-35 quantified in a liquid scintillation counter. The assay provides relative potency ($EC_{50}$ values) and maximum effect (efficacy, $E_{max}$). Antagonist activity is detected as rightward shifts in the agonist dose-response curve in the presence of a fixed amount of antagonist. If the antagonist behaves competitively, the affinity of the receptor/antagonist pair ($K_i$) can be determined. The assay is described in Davis, M. D., J. J. Clemens, T. L. Macdonald and K. R. Lynch (2005) "S1P Analogs as Receptor Antagonists" Journal of Biological Chemistry, vol. 280, pp. 9833-9841.

Example 22

Lymphopenia Assay

The test compounds (e.g., primary alcohols) are dissolved in 2% hydroxypropyl beta-cyclodextrin and introduced into groups of mice by oral gavage at doses from 0.01, 1.0 and 10 mg/kg body weight. At intervals, e.g., 24 hours, 48 hours, or 96 hours the mice are lightly anesthetized and ca. 0.1 mL of blood is drawn from the orbital sinus. The number of lymphocytes (in thousands per microliter of blood; normal is 4-11) is determined using a Hemavet blood analyzer.

Example 23

Heart Rate Assay

Mice are dosed with test compounds (intravenous, 3 mg/kg) or vehicle (2% hydroxypropyl beta-cyclodextrin) and the heart rate measured at 1 hour post dosing. Heart rate is captured in unrestrained, conscious animals using the ECG-enie™ system.

The invention should not be construed to be limited solely to the assays and methods described above, but should be construed to include other methods and assays as well. Other methods that are used but not described above are well known and within the competence of one of ordinary skill in the art of chemistry, biochemistry, molecular biology, and clinical medicine. One of ordinary skill in the art will know that other assays and methods are available to perform the procedures described above.

The abbreviations used above have their conventional meaning within the clinical, chemical, and biological arts. In the case of any inconsistencies, the present disclosure, including any definitions therein will prevail.

The disclosures of each patent, patent application, and publication cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

We claim:

1. A compound of Formula IA, IB, or IC:

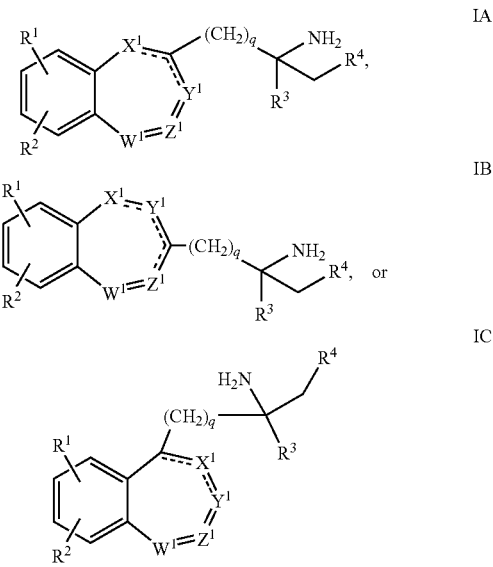

wherein $W^1$, $X^1$, $Y^1$ and $Z^1$ are independently O, $CR^a$, $CR^aR^b$, N, $NR^c$, or S;

$R^1$ and $R^2$ are independently hydrogen, halo, halo($C_1$-$C_{10}$)alkyl, cyano, —$NR^aR^b$, ($C_1$-$C_{20}$)alkyl, ($C_2$-$C_{20}$)alkynyl, ($C_1$-$C_{20}$)alkoxy, ($C_2$-$C_{26}$)alkoxyalkyl, ($C_3$-$C_{12}$)cycloalkyl, ($C_6$-$C_{10}$)aryl, ($C_7$-$C_{30}$)arylalkyl, ($C_2$-$C_{10}$)heterocyclic, ($C_4$-$C_{10}$)heteroaryl, or ($C_4$-$C_{10}$)heteroaryl($C_1$-$C_{20}$)alkyl;

wherein the alkyl, alkenyl, alkynyl, cycloalkyl, aryl, heterocyclic, or heteroaryl groups of $R^1$ and $R^2$ independently are optionally perfluorinated or optionally substituted with 1, 2, 3, or 4 groups where the substituent groups are independently hydroxy, halo, cyano, ($C_1$-$C_{10}$)alkoxy, $C_6$-aryl, ($C_7$-$C_{24}$)arylalkyl, oxo (=O), or imino (=$NR^d$), wherein one or more of the carbon atoms in the $R^1$ or $R^2$ alkyl groups can be independently replaced with non-peroxide oxygen, sulfur or $NR^c$; the alkyl groups of $R^3$ are optionally substituted with 1, or 2 hydroxyl groups; or $R^2$ can be a group having formula II, III, IV, V, or VI;

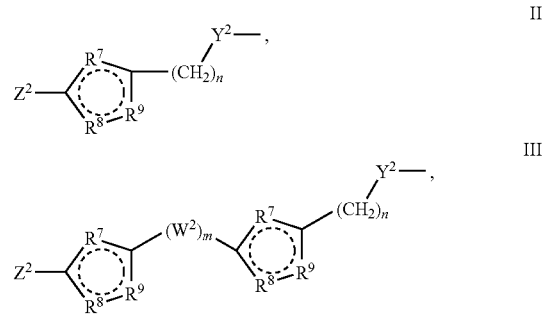

-continued

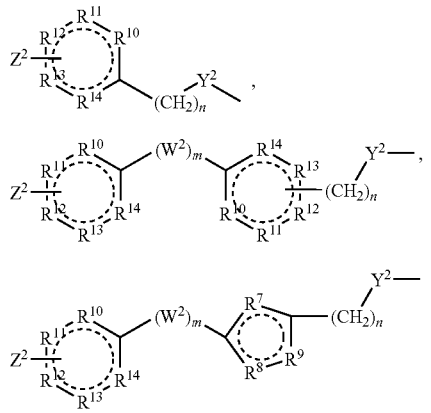

wherein each $R^7$, $R^8$, $R^9$, $R^{10}$, $R^{11}$, $R^{12}$, $R^{13}$, and $R^{14}$ is independently O, S, C, $CR^{15}$, $CR^{16}R^{17}$, C=O, N or $NR^{18}$;

each $R^{15}$, $R^{16}$ and $R^{17}$ is independently hydrogen, halo, $(C_1-C_{10})$alkyl, $(C_6-C_{10})$aryl, $(C_1-C_{10})$alkyl substituted with halo, hydroxy, $(C_1-C_{10})$alkoxy, or cyano; and where $R^{18}$ can be hydrogen or $(C_1-C_{10})$alkyl;

$Z^2$ is hydrogen, halo, halo$(C_1-C_{10})$alkyl, cyano, —$NR^aR^b$, $(C_1-C_{20})$alkyl, $(C_2-C_{20})$alkenyl, $(C_2-C_{20})$alkynyl, $(C_1-C_{20})$alkoxy, $(C_2-C_{26})$alkoxyalkyl, $(C_3-C_{12})$-cycloalkyl, $(C_6-C_{10})$aryl, $(C_7-C_{30})$arylalkyl, $(C_2-C_{10})$heterocyclic, $(C_4-C_{10})$heteroaryl, or $(C_4-C_{10})$heteroaryl$(C_1-C_{20})$ alkyl;

the alkyl, alkenyl, alkynyl, cycloalkyl, aryl, heterocyclic, or heteroaryl groups of $Z^2$ are optionally perfluorinated or optionally substituted with 1, 2, 3, or 4 groups where the substituent groups are independently hydroxy, halo, cyano, $(C_1-C_{10})$alkoxy, $C_6$-aryl, $(C_7-C_{24})$arylalkyl, oxo (=O), or imino (=$NR^d$), wherein one or more of the carbon atoms in the $Z^2$ alkyl groups can be independently replaced with non-peroxide oxygen, sulfur or $NR^c$;

⌒ indicates one or more optional double bonds;

$Y^2$ is a bond (absent), O, S, C=O, or $NR^c$, $CH_2$; $W^2$ is a bond; —$CH_2$— and m is 1, 2, or 3, or $W^2$ is (C=O) $(CH_2)_{1-5}$ and m is 1; wherein $W^2$ is optionally interrupted with non-peroxide O, S, C=O, or $NR^c$;

n is 0, 1, 2, or 3; each ⎯⎯ represents an optional double bond; and q is 0, 1, 2, or 3;

$R^3$ is hydrogen, $(C_1-C_{10})$alkyl, hydroxy$(C_1-C_{10})$alkyl or $(C_1-C_{10})$alkoxy; and $R^4$ is hydroxyl (—OH), phosphate (—$OPO_3H_2$), phosphonate (—$CH_2PO_3H_2$), alpha-substituted phosphonate;

each $R^a$, $R^b$, $R^c$, and $R^d$ is independently hydrogen, $CF_3$ or $(C_1-C_{10})$alkyl; or a pharmaceutically acceptable salt or ester thereof.

2. The compound of claim 1, wherein $R^1$ is hydrogen, fluorine, chlorine, bromine, trifluoro-methyl, methoxy, $(C_1-C_6)$alkyl, $(C_1-C_6)$haloalkyl, $(C_1-C_6)$alkyl substituted with, alkoxy or cyano, alkyl-substituted aryl, aryl-substituted alkyl, or aryl-substituted arylalkyl.

3. The compound of claim 2, wherein $R^1$ is hydrogen, trifluoro-methyl, or —$CH_2CF_3$.

4. The compound of claim 2, wherein $R^1$ is benzyl, phenylethyl, or benzyl substituted with methyl.

5. The compound of claim 1, wherein $R^2$ is:

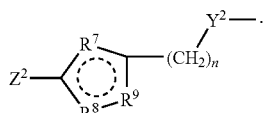

6. The compound of claim 1 wherein $R^2$ is:

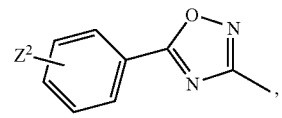

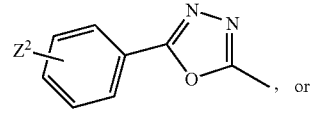

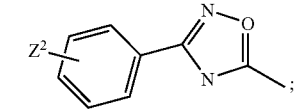

wherein $Z^2$ is $(CH_3)_3C$—, $CH_3CH_2(CH_3)_2C$—, $CH_3CH_2CH_2$—, $CH_3(CH_2)_2CH_2$—, $CH_3(CH_2)_4CH_2$—, $(CH_3)_2CHCH_2$—, $(CH_3)_3CCH_2$—, $CH_3CH_2O$—, $(CH_3)_2CHO$—, or $CF_3CH_2CH_2$— or a group having the formula:

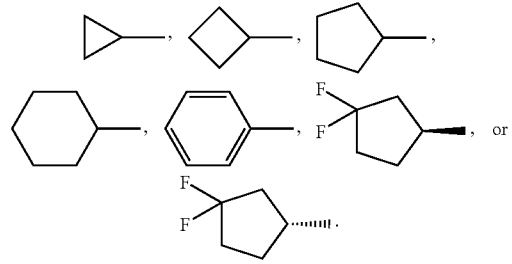

7. The compound of claim 6, wherein $R^2$ is:

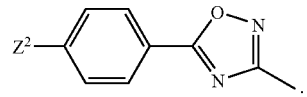

8. The compound of any of claim 1, wherein $R^2$ has Formula III

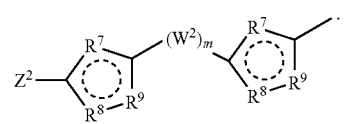

9. The compound of claim 8, wherein $R^2$ is

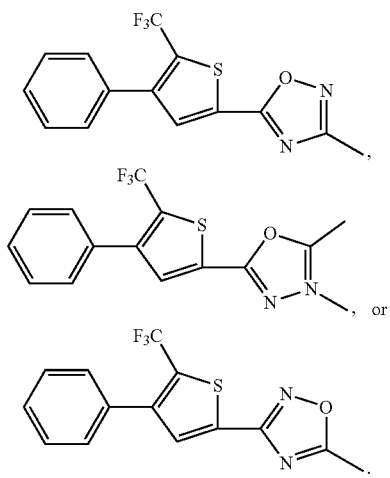

10. The compound of claim 1, wherein $R^2$ is methyl, ethyl, propyl, butyl, pentyl, hexyl, heptyl, octyl, trifluoromethyl, trifluoroethyl, trifluoromethoxy, trifluoroethoxy, methoxy, ethoxy, propoxy, butoxy, pentoxy, heptoxy, or octoxy.

11. The compound of claim 1, wherein each of $X^1$, $Y^1$ and $Z^1$ is $CH_2$.

12. The compound of claim 1, wherein $R^3$ is hydrogen, methyl, hydroxymethyl, ethyl, or hydroxyethyl.

13. The compound of claim 1, having the Formula

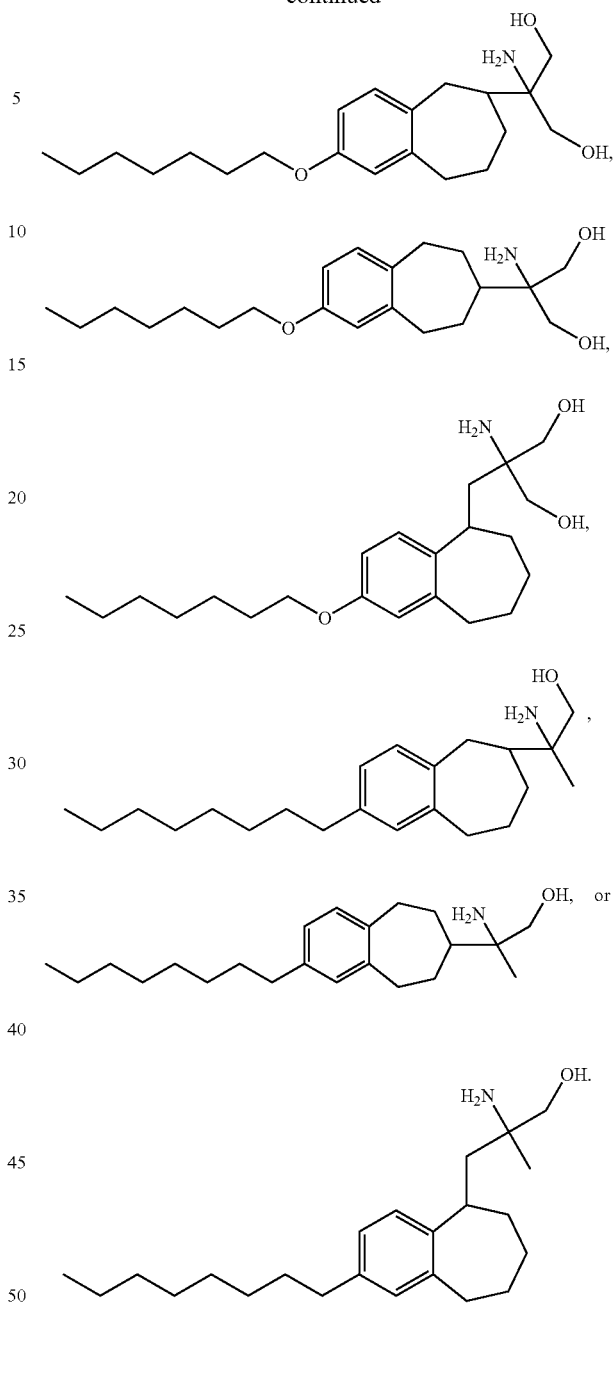

* * * * *